(12) United States Patent
Fontenot et al.

(10) Patent No.: US 11,857,806 B1
(45) Date of Patent: Jan. 2, 2024

(54) LUMINESCENCE-BASED METHOD FOR PRECISE DELIVERY OF ION BEAM THERAPY

(71) Applicant: The United States of America, as represented by the Secretary of the Navy, Arlington, VA (US)

(72) Inventors: Ross S. Fontenot, Montgomery Village, MD (US); William A. Hollerman, Lafayette, LA (US); Noel A. Guardala, Columbia, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 904 days.

(21) Appl. No.: 16/503,095

(22) Filed: Jul. 3, 2019

Related U.S. Application Data

(60) Provisional application No. 62/697,866, filed on Jul. 13, 2018.

(51) Int. Cl.
*A61N 5/10* (2006.01)
*A61B 90/00* (2016.01)

(52) U.S. Cl.
CPC ............ *A61N 5/1049* (2013.01); *A61B 90/39* (2016.02); *A61B 2090/395* (2016.02);
(Continued)

(58) Field of Classification Search
CPC .......... A61N 5/1049; A61N 2005/1051; A61B 90/39; A61B 2090/3937; A61B 2090/3941; A61B 2090/395; A61B 2090/3983
See application file for complete search history.

(56) References Cited

U.S. PATENT DOCUMENTS

| 4,931,653 A | 6/1990 | Hamm et al. |
| 5,006,714 A | 4/1991 | Attix |

(Continued)

OTHER PUBLICATIONS

William A. Hollerman, Ross S. Fontenot, Stephen Williams, and John Miller "Using luminescent materials as the active element for radiation sensors", Proc. SPIE 9838, Sensors and Systems for Space Applications IX, 98380Z (May 13, 2016); https://doi.org/10.1117/12.2228934. Accessed Sep. 26, 2022. (Year: 2016).*

(Continued)

*Primary Examiner* — Carrie R Dorna
(74) *Attorney, Agent, or Firm* — Howard Kaiser

(57) ABSTRACT

Exemplary inventive practice implements Europium Tetrakis Dibenzoylmethide Triethylammonium ($EuD_4TEA$) so as to administer ion beam therapy with extreme precision. An $EUD_4TEA$-inclusive marker (e.g., a solid or gel) is exactingly placed on the skin of a patient in accordance with a predetermined location of cancerous tissue beneath the skin. An ion beam aimed at the $EUD_4TEA$-inclusive marker results in luminescence of at least a portion of the $EUD_4TEA$-inclusive marker, thereby indicating that at least a portion of the ion beam is traveling through the $EUD_4TEA$-inclusive marker and striking the cancer therebelow. According to other modes of exemplary inventive practice, a medical phantom contains a tumor replica that is visibly contrastive inside the medical phantom in terms of luminescence versus non-luminescence. The tumor replica is targeted in ion beam testing to discern optimal geometric and radiative conditions for treating a correspondingly situated patient on the same treatment couch.

9 Claims, 10 Drawing Sheets

(52) U.S. Cl.
CPC .............. *A61B 2090/3941* (2016.02); *A61N 2005/1051* (2013.01); *A61N 2005/1076* (2013.01); *A61N 2005/1087* (2013.01)

(56) References Cited

U.S. PATENT DOCUMENTS

| | | | |
|---|---|---|---|
| 5,586,824 | A | 12/1996 | Barkyoumb et al. |
| 6,683,318 | B1 | 1/2004 | Haberer et al. |
| 7,338,877 | B1 | 3/2008 | Meyer et al. |
| 7,636,419 | B1 | 12/2009 | Nelson |
| 7,657,301 | B2 | 2/2010 | Mate et al. |
| 7,657,302 | B2 | 2/2010 | Mate et al. |
| 7,657,303 | B2 | 2/2010 | Mate et al. |
| 8,222,604 | B2 | 7/2012 | McGill et al. |
| 8,244,330 | B2 | 8/2012 | Meier et al. |
| 8,340,742 | B2 | 12/2012 | Meier et al. |
| 8,402,896 | B1 | 3/2013 | Hollerman et al. |
| 8,437,449 | B2 | 5/2013 | Riley et al. |
| 8,466,428 | B2 | 6/2013 | Iwata |
| 8,674,318 | B2 | 3/2014 | Iwata |
| 8,841,635 | B2 | 9/2014 | Bergeron |
| 9,005,915 | B2 | 6/2015 | Agarwal |
| 9,055,915 | B2 | 6/2015 | Agarwal |
| 9,072,895 | B2 | 7/2015 | Mate et al. |
| 9,238,151 | B2 | 1/2016 | Riley et al. |
| 9,616,248 | B2 | 4/2017 | Meier et al. |
| 9,625,583 | B2 | 4/2017 | Beddar et al. |
| 9,682,253 | B2 | 6/2017 | Meier et al. |
| 10,137,316 | B2 | 11/2018 | Balakin |
| 11,020,616 | B2 | 6/2021 | Engwall et al. |
| 11,052,264 | B2 | 7/2021 | Ranganathan et al. |
| 11,116,459 | B2 | 9/2021 | Dejongh et al. |
| 11,135,451 | B2 | 10/2021 | Raymond et al. |
| 11,235,171 | B2 | 2/2022 | Wulff |
| 11,350,516 | B2 | 5/2022 | Bortfeld et al. |
| 11,351,398 | B2 | 6/2022 | Dempsey et al. |
| 2010/0288916 | A1 | 11/2010 | Cho et al. |
| 2011/0189702 | A1 | 8/2011 | Sun |
| 2016/0049216 | A1 | 2/2016 | Nelson |
| 2017/0281980 | A1 | 10/2017 | Wulff |
| 2017/0322316 | A9 | 11/2017 | Nelson |
| 2021/0387022 | A1 | 12/2021 | Raymond et al. |
| 2022/0054096 | A1 | 2/2022 | DeJongh |

OTHER PUBLICATIONS

U.S. Appl. No. 62/697,866, filed Jul. 13, 2018, Navy case No. 105,643, entitled "Luminescence-Based Method for Precise Delivery of Ion Beam Therapy," listed inventors Ross S. Fontenot, William A. Hollerman, Noel A. Guardala, and Stephen A. Williams.
Stephen Alexander Williams, "Half-Brightness Measurements of Candidate Radiation Sensors," Master's Thesis, a Thesis Presented to the Graduate Faculty of the University of Louisiana at Lafayette in Partial Fulfillment of the Requirements for the Degree Master of Science, 108 pages, University of Louisiana at Lafayette, Summer 2016, published by ProQuest LLC,, ProQuest Dissertations and Theses, publication No. AAT 10163329 (2016).
William A. Hollerman, Ross S. Fontenot, Stephen Williams, and John Miller, "Using Luminescent Materials As the Active Element for Radiation Sensors," Proceedings of SPIE vol. 9838, 98380Z, in Sensors and Systems for Space Applications IX, edited by Khanh D. Pham and Genshe Chen, SPIE, Baltimore, MD, USA, Apr. 19, 2016.
William A. Hollerman (corresponding author), Ross S. Fontenot, Paul Darby, and Nick Pugh (authors), "J01-1784: Potential of Using EuD4TEA for Space-Based Damage and Radiation Sensors," The Electrochemical Society, Wednesday Oct. 4, 2017, 232nd ECS Meeting, National Harbor, MD, Oct. 1-5, 2017.
Ross S. Fontenot, Kamala N. Bhat, William A. Hollerman, and Mohan D. Aggarwal, "Triboluminescent Materials for Smart Sensors," Materials Today, vol. 14, Issue 6, 292-293 (Jun. 2011).
Ross S. Fontenot, William A. Hollerman, Kamala N. Bhat, and Mohan D. Aggarwal, "Comparison of the Triboluminescent Properties for Europium Tetrakis and ZnS:Mn Powders," Journal of Theoretical and Applied Physics 2012, 6:15, http://www.jtaphys.com/content/6/1/15.
William A. Hollerman, Ross S. Fontenot, Kamala N. Bhat, and Mohan D. Aggarwal, "Measuring the Process Variability in Triboluminescence Emission Yield for EuD(4)TEA," Measuring the Process Variability in Triboluminescence Emission Yield for EuD4TEA, Metallurgical and Materials Transactions A, vol. 43A, Nov. 2012, © 2012 The Minerals, Metal & Materials Society and ASM International.
Ross S. Fontenot, William A. Hollerman, Kamala N. Bhat, Mohan D. Aggarwal, and Benjamin G. Penn, "Incorporating Strongly Triboluminescent Europium Dibenzoylmethide Triethylammonium into Simple Polymers," Polymer Journal, vol. 46, pp. 111-116, 2014, published online Sep. 18, 2013, www.nature.com/pj.
Kamala N. Bhat, Ross S. Fontenot, William A. Hollerman, and Mohan D. Aggarwal, "Optimizing the Synthesis of Europium Dibenzoylmethide Triethylammonium," Abstract #3906, Honolulu PRiME 2012, Oct. 7-12, 2012, © 2012 The Electrochemical Society.
W.A. Hollerman, S.M. Goedeke, R.J. Moore, L.A. Boatner, S.W. Allison, and R.S. Fontenot, "Unusual Fluorescence Emission Characteristics From Europium-Doped Lead Phosphate Glass Caused by 3 MeV Proton Irradiation," 2007 IEEE Nuclear Science Symposium Conference Record, N24-180, pp. 1368-1372.
William A. Hollerman, Ross S. Fontenot, Stephen Williams, Naresh Deoli, Armin B. DeVera, and John Miller, "New Half Brightness Fluence Measurements for Large-Grained ZnS:Mn, EuD4TEA, and MgD4TEA Samples," 25th International Conference on the Application of Accelerators in Research and Industry, AIP Conference Proceedings. 2160, 060005 (2019), published by AIP Publishing, 060005-1-06005-10, published online Oct. 2, 2019.
Kamala N. Bhat, Ross S. Fontenot, William A. Hollerman, and Mohan D. Aggarwal, "Triboluminescent Research Review of Europium Dibenzoylmethide Triethylammonium (EuD4TEA) and Related Materials," International Journal of Chemistry, vol. 1 (1), Jan.-Mar. 2012, editor-in-chief D.V.Prabhu, pp. 100-118.
William A. Hollerman, Ross S. Fontenot, Paul Darby, Nick Pugh, John Miller, "Using Exotic Materials Like Eud4tea and Mgd4tea to Monitor Damage and Radiation Exposure in Extreme Environments," The Electrochemical Society (ECS), ECS Transactions, vol. 85, No. 13, 1615, Jun. 2018, 233rd ECS Meeting, Seattle, WA, May 13-17, 2018.
W.A. Hollerman, R.S. Fontenot, S. Williams, and J. Miller, "Using Luminescent Materials As the Active Element for Radiation Sensors," Proceedings SPIE 9838, in Sensors and Systems for Space Applications IX, edited by K.D. Pham and G. Chen, SPIE, Baltimore, MD, USA, Apr. 19, 2016, 98380Z.
R.S. Fontenot, Kamala N. Bhat, William A. Hollerman, and Mohan D. Aggarwal, "Europium Tetrakis Dibenzoylmethide Triethylammonium: Synthesis, Additives, and Applications," Chapter 7 (pp. 147-235) in Triboluminescence: Theory, Synthesis, and Application, editors David O. Olawale, Okenwa O.I. Okoli, Ross S. Fontenot, and William A. Hollerman, Springer International Publishing, Cham, Switzerland (2016).
William A. Hollerman, Ross S. Fontenot, "Using EUD4TEA As the Active Element for Space-Based Radiation Sensors," NASA Human Research Program Investigators' Workshop (2014), 3018.pdf, https://three.jsc.nasa.gov/ws/25/posterSessions/3018.pdf.
Edward W. Collings, Lanchun Lu, Nilendu Gupta, and Mike D. Sumption, "Accelerators, Gantries, Magnets and Imaging Systems for Particle Beam Therapy: Recent Status and Prospects for Improvement Frontiers in Oncology," www.frontiersin.org, Feb. 1, 2022, vol. 11, Article 737837.
"Getting External Beam Radiation Therapy," written byThe American Cancer Society medical and editorial content team (www.cancer.org/cancer/acs-medical-content-and-news-staff.html), last Revised Apr. 10, 2022.
Hirohiko Tsujii, Overview of Carbon-ion Radiotherapy, 2017 J. Phys.: Conf. Ser. 777 012032 IOP Conf. Series: Journal of Physics: Conf. Series 777 (2017) 012032 IOP Publishing.

(56) References Cited

OTHER PUBLICATIONS

"Particle therapy," Wikipedia website, retrieved from https://en.wikipedia.org/w/index.php?title=Particle_therapy&oldid=1072278209, this page was last edited on Feb. 16, 2022, at 21:34 (UTC).
Bob Barnett, "The Next Frontiers in Cancer Therapies," https://www.cancerhealth.com/article/damon-runyon-next-frontiers-cancer-therapies © 2022 Smart + Strong, Aug. 22, 2019 (attached copy is sans graphics).
Casey Halter, "Carbon Ion Therapy: Why This Cancer Treatment Isn't Available in the U.S.," https://www.cancerhealth.com/article/carbon-ion-therapy-cancer-treatment-available-us © 2022 Smart + Strong, Sep. 4, 2019 (attached copy is sans graphics).
Yoshitaka Matsumoto, Nobuyoshi Fukumitsu, Hitoshi Ishikawa, Kei Nakai, and Hideyuki Sakurai, "A Critical Review of Radiation Therapy: From Particle Beam Therapy (Proton, Carbon, and BNCT) to Beyond," Journal of Personalized Medicine 2021, 11, 825 https://www.mdpi.com/journal/jpm.

\* cited by examiner

| Phosphor | | Sample Form | Irradiation Energy (MeV) | $N_{1/2}$ (mm$^{-2}$) |
| --- | --- | --- | --- | --- |
| Material | Dopant | | | |
| YAG | Ce | PC Paint | 3 | $(1.28 \pm 0.21) \times 10^{14}$ |
| | | Single Crystal | 3 | $(4.03 \pm 0.65) \times 10^{14}$ |
| | | Pressed Cellulose Tablet | 3 | $(0.11 \pm 0.01) \times 10^{14}$ |
| $Y_2O_2S$ | Eu | PC Paint | 3 | $(0.60 \pm 0.46) \times 10^{14}$ |
| $Gd_2O_2S$ | Pr | PC Paint | 3 | $(0.16 \pm 0.11) \times 10^{14}$ |
| | Tb | PC Paint | 3 | $(0.20 \pm 0.13) \times 10^{14}$ |
| $Y_2SiO_5$ | Ce | Single Crystal | 3 | $(0.28 \pm 0.01) \times 10^{14}$ |
| $Tb_3Ga_5O_{12}$ | None | Single Crystal | 3 | $(0.12 \pm 0.01) \times 10^{14}$ |
| ZnS | Mn | PC Paint | 3 | $(0.92 \pm 0.07) \times 10^{14}$ |
| | | 30 μm Thick Paint | 1 | $(0.18 \pm 0.01) \times 10^{14}$ |
| | | | 3 | $(0.22 \pm 0.01) \times 10^{14}$ |
| | | 10.5 μm PMMA | 3 | $(0.49 \pm 0.07) \times 10^{14}$ |
| $EuD_4TEA$ | None | Thick Paint | 3 | $(2.83 \pm 0.19) \times 10^{10}$ |

FIG. 1

| MARKER | SOLID MARKER | GELATINOUS MARKER | ATTACHED OR APPLIED TO HUMAN SKIN | ATTACHED OR APPLIED TO, OR EMBEDDED IN, AN EUD$_4$TEA-INCLUSIVE COVERING FORM | ATTACHED OR APPLIED TO, OR EMBEDDED IN, AN EUD$_4$TEA-EXCLUSIVE COVERING FORM | ATTACHED OR APPLIED TO, OR EMBEDDED IN, AN EUD$_4$TEA-INCLUSIVE PHANTOM FORM | ATTACHED OR APPLIED TO, OR EMBEDDED IN, AN EUD$_4$TEA-EXCLUSIVE PHANTOM FORM |
|---|---|---|---|---|---|---|---|
| EUD$_4$TEA-INCLUSIVE MARKER | X | X | X |  | X |  | X |
| EUD$_4$TEA-EXCLUSIVE MARKER | X |  |  | X |  | X |  |

LUMINESCENCE-BASED METHOD FOR PRECISE DELIVERY OF ION BEAM THERAPY

CROSS-REFERENCE TO RELATED APPLICATIONS

This application claims the benefit of U.S. provisional application No. 62/697,866, filed 13 Jul. 2018, hereby incorporated herein by reference, entitled "Luminescence-Based Method for Precise Delivery of Ion Beam Therapy," joint inventors Ross S. Fontenot, William A. Hollerman, Noel A. Guardala, and Stephen A. Williams.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

The present invention relates to cancer and oncology, more particularly to methods, systems, and devices for administering radiation therapy for cancer treatment.

Conventional radiation therapy for defeating cancer involves the directing of x-rays or gamma rays so as to impinge upon a cancer target (such as a tumor) in a human body. Such external beam radiation therapy is often effective in destroying cancerous tissue, but an unwanted concomitant is the destruction of healthy tissue. Inevitably, when conventional radiation is focused upon a cancer target, both cancerous cells and healthy cells that are in the vicinity of the cancerous cells are destroyed.

Conventional radiotherapy, by its very nature, cannot be directed at cancerous tissue with sufficient precision to completely avoid destruction of nearby non-cancerous tissue. X-ray and gamma ray emanations are too diffuse to hit targets with pinpoint accuracy. The intensity of conventional therapy radiation tends to spread out and gradually weaken over distance in space. Another conventional cancer therapy is chemotherapy; this too is purposed to destroy malignant tissue but at the same time is deleterious to normal tissue.

Conventional radiation therapy is characterized by emission of photons. A newer kind of external beam radiation therapy against cancer, known as ion beam therapy, is characterized by emission of ions (charged particles). As compared to conventional radiation therapy, ion beam radiation therapy is advantageous in its superior ability to attack cancerous tissue while circumventing healthy tissue. Ion beam therapy can be administered more selectively than conventional radiotherapy and potentially affords pinpoint accuracy. Unfortunately, ion beam therapy is considerably more expensive than conventional radiation therapy, and the progress of ion beam therapy in oncologic practice has thus been impeded by economic considerations. Many medical experts believe that ion beam therapy should be considerably more accessible and affordable than it is at the present time.

The lightest ion is a hydrogen ion, which is a proton. Proton beam therapy is the most common type of ion beam therapy, but heavy ion beams are making inroads in oncology. Heavier ions such as helium, boron, carbon, and neon have been investigated for implementation in ion beam therapy. Radiation for particle radiation oncology is obtained by accelerating charged nuclei. In proton beam therapy, the charged nuclei are the nuclei of hydrogen atoms (i.e., protons). In heavy ion beam therapy, the charged nuclei are nuclei of atoms heavier than hydrogen; hence, the charged nuclei of heavy ions are heavier than protons. The term "ion beam therapy" (synonymously, "ion beam radiation therapy"), as used herein, broadly encompasses both proton beam therapy and heavy ion beam therapy.

Carbon-ion beam therapy has taken the lead in heavy-ion beam therapy, as carbon ions have demonstrated greater stability and versatility than the other heavy ions. Generally, heavy ions are better than protons for defeating cancers requiring greater targeting precision and/or greater doses of radiation. Protons tend to scatter more than heavy ions and to be delivered with less exactitude over spatial ranges. Because of their greater mass, heavy ions tend to scatter less and more completely remain in the intended direction. However, economics again plays a role, as heavy ion therapy costs more than proton therapy.

SUMMARY OF THE INVENTION

In view of the foregoing, an object of the present invention is to provide a new and improved methodology for delivering radiation treatment to selectively destroy malignant cells in a human or animal.

Another object of the present invention is to provide such a methodology for administering ion beam therapy, wherein a recognized increase in effectiveness of ion beam therapy results generally in a medical policy shift toward perceiving ion beam therapy as justifying its costs.

In accordance with exemplary practice of the present invention, a method for administering radiation therapy to a human or other animal includes (a) placing an $EUD_4TEA$-inclusive marker on an area of skin, and (b) directing an ion beam toward the $EUD_4TEA$-inclusive marker so that at least a portion of the $EUD_4TEA$-inclusive marker luminesces. The placing of the $EUD_4TEA$-inclusive marker is performed in accordance with a location of cancer. The luminescence of the at least a portion of the $EUD_4TEA$-inclusive marker is associated with impingement of the ion beam upon the $EUD_4TEA$-inclusive marker. The directing of the ion beam is performed so that at least a portion of the ion beam passes through the $EUD_4TEA$-inclusive marker and impinges upon the cancer.

An exemplary inventive method for designing radiation therapy includes positioning a combination including two components, viz., a medical phantom and a tumor reproduction contained in the medical phantom. A first component of the combination is $EUD_4TEA$-inclusive and a second component of the combination is $EUD_4TEA$-exclusive. The exemplary inventive method for designing radiation therapy further includes directing an ion beam toward the combination so that the ion beam impinges upon the tumor reproduction. The impingement of the ion beam upon the tumor reproduction is appreciable based on contrast between a visibility of the ion beam in the first component and an invisibility of the ion beam in the second component. If the first component is the medical phantom and the second component is the tumor reproduction, then the ion beam is visible in the medical phantom due to $EUD_4TEA$ luminescence, and the ion beam ceases to be visible upon impinging upon the tumor reproduction. If the first component is the tumor reproduction and the second component is the medical phantom, then the ion beam is invisible in the medical phantom, and the ion beam is visible in the tumor reproduction due to $EUD_4TEA$ luminescence.

According to some exemplary embodiments of the present invention, a method for performing radiation treatment includes (a) introducing an EUD$_4$TEA-inclusive material into at least one vessel in a tumorous region of a patient, and (b) directing an ion beam toward the tumorous region so that at least a portion of the EUD$_4$TEA-inclusive material luminesces in the at least one vessel.

The present invention, as exemplarily embodied, represents a novel methodology for administering external beam radiotherapy. Featured by the present invention is, inter alia, an implementation of EuD$_4$TEA that takes advantage of unique properties of EuD$_4$TEA. In particular, EuD$_4$TEA is inventively implemented to serve as a beacon for proton therapy and other kinds of particle therapy. EuD$_4$TEA responds heavily to protons, but does not respond to other forms of radiation such as photons or neutrons.

According to accepted medical usage of the term "ion therapy," a patient undergoing ion beam therapy encounters protons (e.g., hydrogen ions) or heavier ions (e.g., carbon ions). The term "hadron therapy" is sometimes used to describe therapy involving neutrons and protons. Ion beam radiation therapy is distinguishable from photon beam radiation therapy (e.g., x-ray therapy or gamma ray therapy), which represents by far the most prevalent genre of oncological radiotherapy.

A first category of inventive practice provides for implementation of an EuD$_4$TEA-inclusive marker. Exemplary inventive practice of an EuD$_4$TEA-inclusive marker includes placement thereof atop or next to or attached to a patient's skin. Depending on the inventive embodiment, an EuD$_4$TEA-inclusive marker may be, for example, a solid object that is adhered to a person's skin, or a gelatinous substance that is spread upon a person's skin, or a portion of a covering that fits closely over a person's skin. The present invention's implementation of an inventive EuD$_4$TEA-inclusive marker may be particularly propitious in applications in which a cancerous mass is superficial, i.e., lies at or proximately beneath a patient's skin.

The present invention's implementation of an inventive medical phantom may be particularly propitious in applications in which a cancerous mass lies deeply below the skin. Inventive practice may locate one or more EuD$_4$TEA-inclusive markers anywhere on the body of a human or animal (e.g., head, trunk, or extremity). An inventive practitioner may fine-tune an ion beam by using the resultant luminescence from interaction of an ion beam with a suitably placed EuD$_4$TEA-inclusive marker. For instance, it may be propitious inventive practice to place a gel incorporating EuD$_4$TEA on or near a cancer location, and to then adjust the ion beam directionally and/or magnitudinally, doing so utilizing the light emanating from the EuD$_4$TEA-inclusive gel marker.

Some inventive embodiments provide a medical phantom such as a phantom head, phantom torso, or phantom extremity. The present invention's implementation of an inventive medical phantom may be particularly propitious in applications in which a cancerous mass is not superficial, i.e., lies more deeply beneath the skin. Otherwise expressed, the malignancy is more internal than external. An ion beam (particle beam) that is directed toward the inventive phantom is characterized by an intensity, a three-dimensional direction, and a penetration depth into the phantom, and impinges upon a tumor facsimile situate inside the phantom. The tumor facsimile, inside the inventive phantom, corresponds in shape and location to the tumor of the real-life patient.

An exemplary medical phantom in accordance with the present invention contains EuD$_4$TEA material and one or more facsimile tumors. According to exemplary inventive practice, the EuD$_4$TEA material in the inventive phantom luminesces (e.g., glows a bright red color) in reaction to impingement thereupon of an ion beam. A facsimile of each cancerous tumor is shaped and situated inside the inventive phantom in exact correspondence with a tumor situated inside an actual patient's head or body. An ion beam is directed inside the inventive phantom so as to impinge upon a tumor facsimile. The tumor facsimiles are thus each radiatively focused upon and evaluated, one tumor at a time.

Practitioners of the present invention may perform testing using an inventive phantom in order to select sizes, shapes, positions, settings, and adjustments of inventive markers and particle accelerators. An inventive practitioner thus optimizes the inventive treatment that follows of the real-life patient, particularly in terms of the magnitudes, concentrations, and directions of the ion beams with respect to the cancerous tumors. Inventive phantoms are especially efficacious when inventively used in furtherance of destroying cancerous cells located under a patient's skin at greater than superficial depths inside a patient.

Other modes of inventive practice are possible, especially in the medical realm. For example, some veins in a human are close to the surface of the skin. Exemplary inventive practice may provide for intravenous delivery (e.g., via injection or infusion) of an EuD$_4$TEA-inclusive material (e.g., an EuD$_4$TEA-containing solution) inside a patient's body. At least some of the venal locations that are impinged upon by an ion beam will visibly luminesce. From an external perspective, the luminescence may be more visible in a darkened room. An inventive practitioner may identify vascular tumors and other cancerous target areas and may direct the ion beam therapy accordingly.

BRIEF DESCRIPTION OF THE DRAWINGS

The present invention will now be described, by way of example, with reference to the accompanying drawings, wherein:

FIG. 1 is a tabular representation of proton $N_{1/2}$ data for various phosphor materials and dopants, phosphor forms, and irradiation energies.

FIG. 10 is a tabular representation informative about markers in accordance with the present invention. Various types and uses of inventive markers are denoted.

DESCRIPTION OF EXEMPLARY EMBODIMENTS OF THE INVENTION

Figure 2:
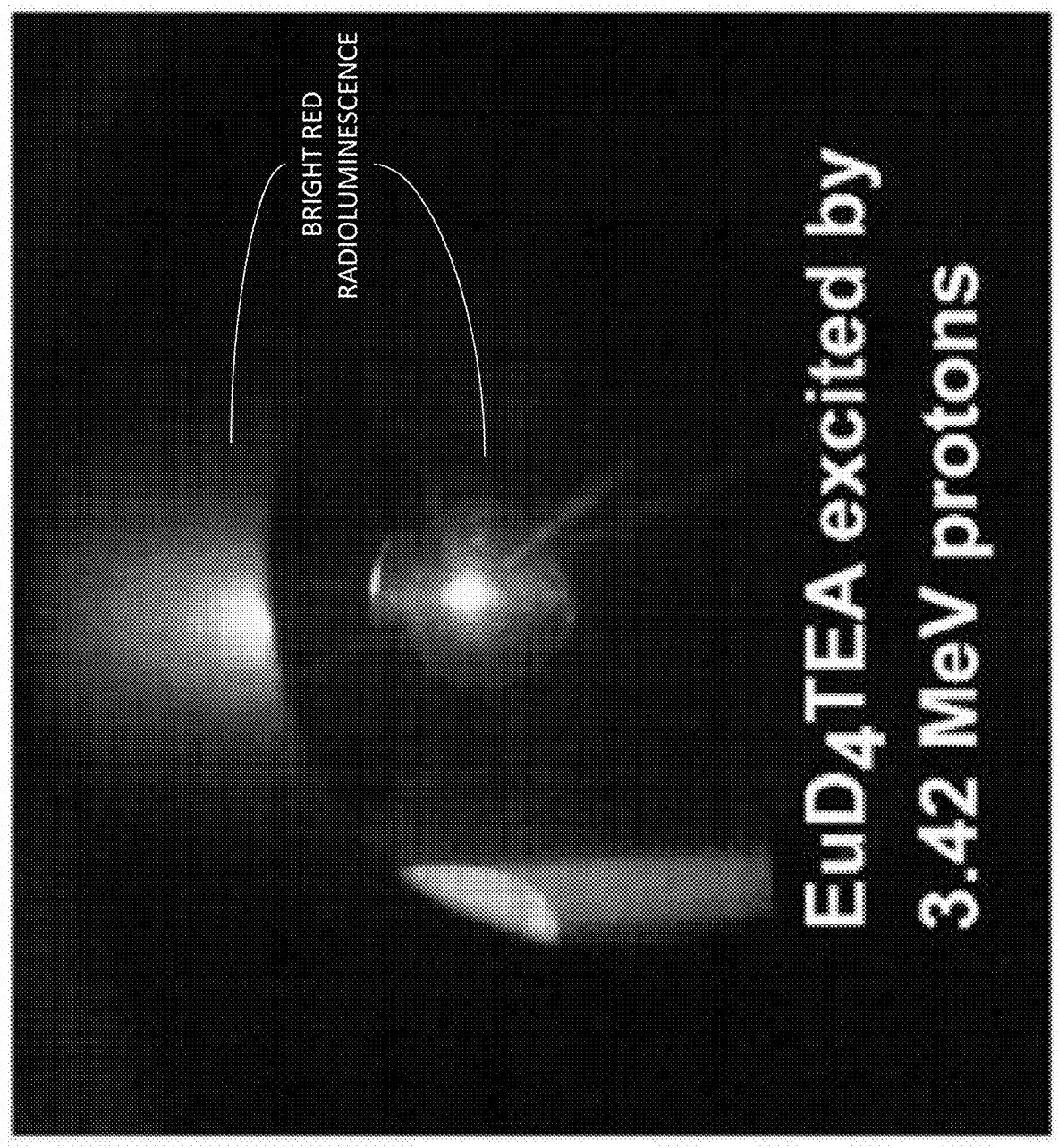
FIG. 2 is a photographic image of an interaction between a proton beam and an EuD$_4$TEA entity, in particular featuring the radioluminescence of the EuD$_4$TEA from 3.42 MeV protons.

Optically stimulated luminescence (OSL) is one of the main types of passive dosimetry. Other types include thermo-luminescence, film, and track-etch dosimetry. Optical stimulation represents a way to retrieve stored energy from materials. OSL materials emit light when stimulated by photons of light; that is, OSL materials store energy but give off light when they are optically stimulated.

In 2010 Ross S. Fontenot and research colleagues began investigating an organic compound known as europium tetrakis dibenzoylmethide triethylammonium ($EuD_4TEA$). See W. A. Hollerman, R. S. Fontenot, K. N. Bhat, M. D. Aggarwal, C. J. Guidry, and K. M. Nguyen, "Comparison of triboluminescent emission yields for 27 luminescent materials," Optical Materials 34(9), 1517-1521 (2012), hereby incorporated herein by reference; see also, R. S. Fontenot, K. N. Bhat, W. A. Hollerman, and M. D. Aggarwal, "Triboluminescent materials for smart sensors," Materials Today, 14, 292-293 (2011), hereby incorporated herein by reference. Fontenot et al. found that triboluminescent emitted from $EuD_4TEA$ is bright enough to be seen in daylight, and has 206% of the emission yield of ZnS:Mn when subjected to low energy impacts.

As distinguished from OSL materials, most materials cannot store energy and in fact are damaged by ionizing radiation. It has been found that both proton radiation and heavier ion radiation reduce the luminescence emitted from both inorganic and organic materials. In 1951, Birks and Black showed experimentally that the fluorescence efficiency of anthracene bombarded by alphas varies with the total fluence as $$\frac{I}{I_0} = \frac{1}{1 + \frac{N}{N_{1/2}}}, \tag{1}$$

where I, $I_0$, N, and $N_{1/2}$ represent the fluorescence emission intensity, initial fluorescence emission intensity, total incident particle fluence, and the half brightness fluence, respectively. J. B. Birks, "Scintillations from Organic Crystals: Specific Fluorescence and Relative Response to Different Radiations," Proc. Phys. Soc. Sect. A 64,874 (1951). The units of I and $I_0$ are related to the number of fluorescence photons interacting with the detector. When plotting the reciprocal of the light ratio ($I_0$/I) versus proton fluence, the resulting curve is linear with the slope equal to the inverse of $N_{1/2}$. The corresponding curve intercept is unity.

Schulman observed an effect similar to Equation (1) when organic anthracene was exposed to gamma irradiation. J. H. Schulman, H. W. Etzel, and J. G. Allard, "Application of Luminescence Changes in Organic Solids to Dosimetry,"J. Appl. Phys. 28, 792-795 (1957). Black later observed no efficiency degradation when the phosphor was exposed to 40 keV electrons, since they only cause ionization damage with no atomic displacements. F. A. Black, "The Decay in Fluorescence Efficiency of Organic Materials on Irradiation by Particles and Photons," Philos. Mag. Ser. 7 44, 263-267 (1953). Northrop and Simpson found that the fluorescence efficiency deteriorated in a similar fashion as was measured in previous measurements for organic phosphors. D. C. Northrop and O. Simpson, "Electronic Properties of Aromatic Hydrocarbons II: Fluorescence Transfer in Solid Solutions." Proc. R. Soc. London. Ser. A. Math. Phys. Sci. 234, 136-149 (1956).

Broser and Kallmann developed a similar relationship to Equation (1) for inorganic phosphors irradiated using alpha particles. These results indicate that radiation produced quenching centers compete with emission centers for absorbed energy. Von Immanuel Broser und Hartmut Kallmann, "Uber die Anregung von Leuchtstoffen durch schnelle Korpuskularteilchen I (Eine neue Methode zur Registrierung und Energiemessung schwerer geladener Teilchen)," Aus dem Kaiser-Wilhelm-Institut für physikalische Chemie und Elektrochemie, Berlin-Dahlem, Z. Naturforsch, 2A, 439 (1950).

For the past decade researchers have been measuring $N_{1/2}$ for several single crystal polycrystalline paint and pressed tablet forms of selected rare earth phosphors prepared at ambient temperature. FIG. 1 is a tabular representation of selected proton $N_{1/2}$ data for several phosphor materials and forms. As shown in FIG. 1, the resulting $N_{1/2}$ values vary in the range between $2.83 \times 10^{10}$ to $4.03 \times 10^{14}$ $mm^{-2}$. The term "PC Paint" refers to PPMS paint with polycrystalline phosphor. The term "Thick Paint" refers to thick PPMS paint with larger grained (size shown) polycrystalline phosphor. The term "Single Crystal" refers to a single slice of the given phosphor crystal. These phosphors emitted light by radioluminescence that were excited by using a 1 or 3 MeV proton beam from a small electrostatic accelerator.

The data shown in FIG. 1 is taken from the following references: W. A. Hollerman, S. W. Allison, S. M. Goedeke, P. Boudreaux, R. Guidry, and E. Gates, "Comparison of Fluorescence Properties for Single Crystal and Polycrystalline YAG:Ce," *Nucl. Sci. IEEE Trans.* 50, 754-757 (2003); W. A. Hollerman, N. P. Bergeron, F. N. Womack, S. M. Goedeke, and S. W. Allison, "Changes in Half Brightness Dose Due to Preparation Pressure for YAG:Ce," *Nucl. Sci. IEEE Trans.* 51, 1080-1083 (2004); W. A. Hollerman, J. H. Fisher, L. R. Holland, and J. B. Czirr, "Spectroscopic Analysis of Proton-Induced Fluorescence from Yttrium Orthosilicate," *Nucl. Sci. IEEE Trans.* 40, 1355-1358 (1993); W. A. Hollerman, J. H. Fisher, D. Ila, G. M. Jenkins, and L. R. Holland, "Proton-Induced Fluorescence Properties of Terbium Gallium Garnet,"*J. Mater. Res.* 10, 1861-1863 (1995); W. A. Hollerman, S. M. Goedeke, N. P. Bergeron, R. J. Moore, S. W. Allison, and L. A. Lewis, "Emission Spectra from ZnS:Mn due to Low Velocity Impacts," in *Photonics Sp. Environ. X*, edited by E. W. Taylor (SPIE, San Diego, CA, USA, 2005), 58970E-10; W. A. Hollerman, S. M. Goedeke, N. P. Bergeron, C. I. Muntele, S. W. Allison, and D. Ila, "Effects of Proton Irradiation on Triboluminescent Materials such as ZnS:Mn," *Nucl. Instruments Methods Phys. Res. Sect. B Beam Interact. with Mater. Atoms* 241, 578-582 (2005); W. A. Hollerman, S. M. Goedeke, R. J. Moore, L. A. Boatner, S. W. Allison, and R. S. Fontenot, "Unusual Fluorescence Emission Characteristics from Europium-Doped Lead Phosphate Glass Caused by 3 MeV Proton Irradiation," in 2007 *IEEE Nucl. Sci. Symp.* (IEEE, Honolulu, H I, 2007), 1368-1372; F. N. Womack, S. M. Goedeke, N. P. Bergeron, W. A. Hollerman, and S. W. Allison, "Measurement of Triboluminescence and Proton Half Brightness Dose for ZnS:Mn," *IEEE Trans. Nucl. Sci.* 51, 1737-1741 (2004); W. A. Hollerman, R. S. Fontenot, S. Williams, and J. Miller, "Using Luminescent Materials as the Active Element for Radiation Sensors," *Proceedings SPIE 9838*, in *Sensors and Systems for Space Applications IX*, edited by K. D. Pham and G. Chen (SPIE, Baltimore, MD, USA, 19 Apr. 2016), 98380Z; W. A. Hollerman, G. A. Glass, and S. A. Allison, "Survey of Recent Research Results for New Fluor Materials, "*MRS Online Proc. Libr.* 560, 335-341 (1999); Stephen A. Williams, *Half Brightness Measurements of Candidate Radiation Sensors*, Master's Thesis, University of Louisiana at Lafayette, August 2016.

Still referring to FIG. 1, the binder used for most of the polycrystalline samples were (phenyl methyl) siloxane (PPMS) and PMMA. Samples labeled "PC Paint" had phosphor grain sizes that were measured to be less than 10 μm. These materials were applied to an aluminum substrate using a standard airbrush with a paint containing approximately 70% PPMS and 30% phosphor powder; this formulation was found to give the toughest and most wear resistant paint. Samples labeled "Thick Paint" also used PPMS as a binder. However, these paints were too thick and the phosphor grains were too large to be sprayed using the airbrush; therefore, these paint materials were spread on an aluminum substrate in much the same way that jam is applied to bread. Small phosphor crystal slices were mounted directly to the sample holder for measurement. Proton beam current was kept small to minimize electrical discharge.

With one exception, the Birks and Black relation describes the reduction in fluorescence yield for all inorganic materials tested between 1990 and the present. In that exceptional case, the emitted radioluminescence yield from a lead phosphate glass doped with 6 wt. % europium sample increased linearly to a maximum tested fluence of about $10^{15}$ mm$^{-2}$. W. A. Hollerman, S. M. Goedeke, R. J. Moore, L. A. Boatner, S. W. Allison, and R. S. Fontenot, "Unusual Fluorescence Emission Characteristics from Europium-Doped Lead Phosphate Glass Caused by 3 MeV Proton Irradiation," *IEEE Nuclear Science Symposium Conference Record*, Honolulu, Hawaii, 1368-1372 (2007), cited hereinabove. This "de facto" implantation could have changed its material properties of the glass and hence its band structure. Overall, $N_{1/2}$ appears to be a good figure of merit to evaluate and compare the degradation of emission yield when a phosphor is exposed to ionizing radiation.

Seven materials are listed in FIG. 1, viz.: EuD$_4$TEA, YAG, Y$_2$O$_2$S, Gd$_2$O$_2$S, Y$_2$SiO$_5$, Tb$_3$Ga$_{12}$, and ZnS. With the exception of EuD$_4$TEA, all of the materials listed in FIG. 1 are relatively radiation-resistant and would take a large fluence to reduce the luminescence enough to be useful as a radiation sensor. However, organics are much more sensitive to radiation, as Schulman et al. determined when they investigated the effects of gamma rays and electrons on the photoluminescence of anthracene and naphthalene. J. H. Schulman, H. W. Etzel, and J. G. Allard, *J. Appl. Phys.* 28, 792-795 (1957). In fact, organics can be six orders of magnitude more sensitive than the inorganics. Due to their sensitivity, organics may be useful for low fluence or low dose applications. EuD$_4$TEA appears to be about three orders of magnitude more sensitive than the other inorganic materials shown in FIG. 1. Accordingly, the present inventors believe that EuD$_4$TEA can be used to detect stress/impacts and ionizing radiation at the same time.

Tribble disclosed that a spacecraft at 1 AU from the sun will receive a 1 MeV proton fluence of less than $10^{11}$ mm$^{-2}$ from a large solar event. Likewise, 1 MeV proton fluences in the Earth's radiation belts and the Earth-Moon-Sun Lagrange points will be even less than the $10^{11}$ mm$^{-2}$ value from large solar events. A. C. Tribble, *The Space Environment: Implications for Spacecraft Design*, Princeton University Press, Princeton, NJ (2003). The present inventors concluded therefrom that EuD$_4$TEA, which is characterized by a $N_{1/2}$ of about 2.8×$10^{10}$ mm$^{-2}$, may be a good candidate for use as a personal proton fluence sensor for astronauts in vehicles flying in near earth space.

In 2013, Fontenot et al. investigated the effects of uranium on the triboluminescence of EuD$_4$TEA. Hereby incorporated herein by reference is R. S. Fontenot, W. A. Hollerman, K. N. Bhat, and M. D. Aggarwal, "Effects of Added Uranium on the Triboluminescent Properties of Europium Dibenzoylmethide Triethylammonium," *J. Lumin.* 134, 477-482 (2013). Uranyl acetate, characterized by an activity of 0.2 μCi/g, was added to the synthesis process to determine the effects of uranium on the triboluminescent properties of EuD$_4$TEA. The amount of uranium acetate was varied such that the amount of uranium to europium was 0-100 mol %. After the product formed, they were tested for the triboluminescent properties. The 4 mol % uranium initially increased the triboluminescent yield over the pure EuD$_4$TEA by approximately 80%. The sample was found to have an emission rate that was about twice above the background. However, gains in TL yield decreased with time owing to the emission of radiation from the depleted $^{238}$U in these samples.

The present inventors believe it likely that ionizing radiation emitted from the decay of $^{238}$U and its corresponding daughter products caused the reduction in emission yield that was observed by Fontenot et al. as reported in *J. Lumin.* 134, 477-482 (2013), cited hereinabove. In fact, the reduction in fluorescence intensity upon exposure to ionizing radiation from heavy charged particles appears to be similar to what is described in the Birks and Black relation. See J. B. Birks, "Scintillations from Organic Crystals: Specific Fluorescence and Relative Response to Different Radiations, "*Proc. Phys. Soc. Sect. A* 64, 874 (1951); W. A. Hollerman, N. P. Bergeron, F. N. Womack, S. M. Goedeke, and S. W. Allison, "Changes in Half Brightness Dose Due to Preparation Pressure for YAG:Ce," *Nucl. Sci. IEEE Trans.* 51, 1080-1083 (2004).

These radiation particles break chemical bonds, thus reducing the radiative emission in doped $EuD_4TEA$. After 120 days, results showed that the triboluminescent yield for the 4 mol % doped uranium samples was reduced by approximately 20% over the initial value measured when the sample was synthesized. At this rate, it should take approximately 335 days for the TL yield to be reduced to half of its original value. Fontenot et al., *J. Lumin.* 134, 477-482 (2013), aforecited. This investigation by Fontenot et al. indicated that uranium is a very poor dopant. In the present inventors' view, Fontenot et al.'s investigation also suggested that $EuD_4TEA$ is very sensitive to radiation and would serve as a good low-level real time radiation sensor. In this regard, the present inventors note that $EuD_4TEA$ emits a (very) bright red radioluminescence under ionizing irradiation, such as illustrated in FIG. 2.

In 2016 the present inventors (in particular Hollerman, Guardala, and Fontenot) conducted radiation research including radiation measurements. The present inventors irradiated $EuD_4TEA$ with gamma rays. Their investigation indicated that $EuD_4TEA$ is insensitive to MeV-class photons to a total dose of ~30 Mrad. Furthermore, of particular importance as relates to the present invention, no radioluminescence was observed under gamma irradiation. In addition, the present inventors irradiated $EuD_4TEA$ with ionizing radiation. As depicted by way of example in FIG. 2, $EuD_4TEA$ emitted a bright red light when it was exposed to 3.42 MeV protons, which is a type of ionizing radiation.

Figure 3:
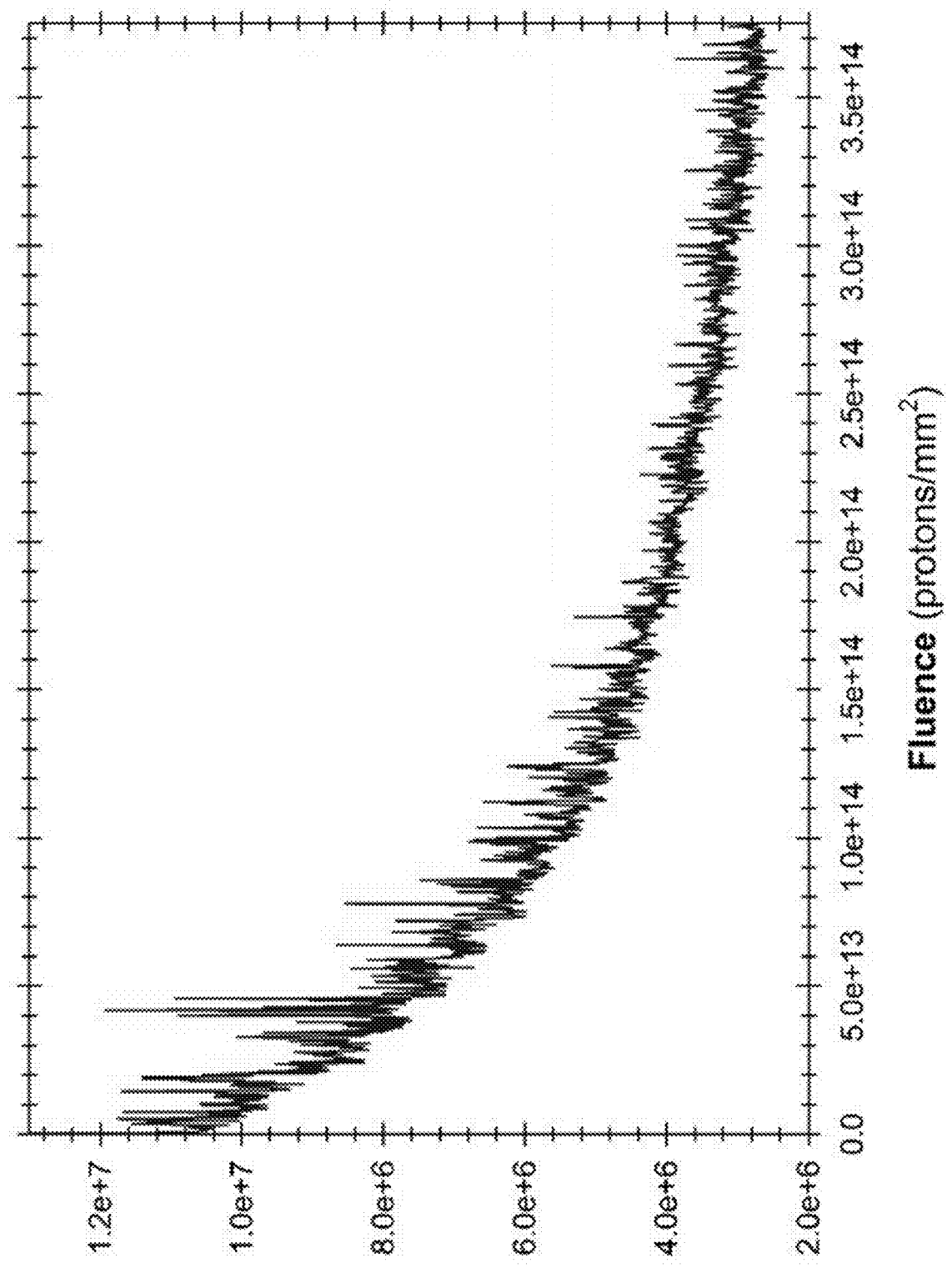
FIG. 3 is a graphical representation of the effect of 3.42 MeV proton fluence on the luminescent emission intensity of EuD$_4$TEA.

As illustrated in FIG. 3, the present inventors determined that the intensity of emission exponentially decreased as the fluence was increased. In fact, it took less than two minutes for the protons to completely quench the luminescence. In contrast, when the present inventors exposed $EuD_4TEA$ to gamma rays, no luminescence was observed. Moreover, by exciting $EuD_4TEA$ with UV light during gamma irradiation, no decrease in luminescence was observed using a standard spectrometer up to ~30 Mrad. Future testing may be conducted by the present inventors to determine whether radioluminescence is observed for electrons and neutrons.

Based on their findings, the present inventors concluded that $EuD_4TEA$ can be used as a visual sensor to detect ionizing radiation. The present invention, as exemplarily embodied, is in principle a visual radiation sensor that is based on the luminescent material europium tetrakis dibenzoylmethide triethylammonium ($EuD_4TEA$). Multifarious modes of operation of an inventive sensor are possible, depending upon the inventive embodiment. The present invention's visual sensor includes a luminescent material that emits radioluminescence in an ionizing radiation environment and produces no light for nonionizing radiation such as gammas.

The term "$EuD_4TEA$-inclusive device," as used herein, broadly refers to a distinct physical collection, quantity, mass, body, object, or structure that includes $EuD_4TEA$. An inventively implemented $EuD_4TEA$-inclusive device can take any of various solid, liquid, or mesophase forms and can have any of various physical properties, e.g., soft, hard, porous, non-porous, rigid, flexible, viscous, non-viscous, gelatinous, transparent, translucent, opaque, etc. Furthermore, an inventively implemented $EuD_4TEA$-inclusive device can partially or fully describe any of various two-dimensional or three-dimensional geometric shapes, regular or irregular or some combination thereof, e.g., circular, ellipsoidal, triangular, rectangular, pentagonal, hexagonal, parallelepiped, rectangular prismatic, pyramidal, etc. The term "$EuD_4TEA$-exclusive device," as used herein, broadly refers to a distinct physical collection, quantity, mass, body, object, or structure that does not include $EuD_4TEA$.

According to exemplary inventive practice, an $EuD_4TEA$-inclusive device is made by combining $EuD_4TEA$ material with a different material, such as by incorporating, mixing, attaching, joining, adhering, casting, coating, molding, weaving, polymerizing, or otherwise associating $EuD_4TEA$ with a non-$EuD_4TEA$ entity. An $EuD_4TEA$-inclusive device is thereby provided that can be viewed or monitored by an inventive practitioner. For instance, $EuD_4TEA$ liquid material may be coated (e.g., painted) onto a non-$EuD_4TEA$ entity. Or, an $EuD_4TEA$-inclusive device can be made through polymerization of $EuD_4TEA$ with a different material. Or, an $EuD_4TEA$ thin film can be deposited on a substrate. Or, a solid $EuD_4TEA$ material can be adhered or otherwise physically attached to a separate entity (such as by using an epoxy adhesive). Or, $EuD_4TEA$ crystals (e.g., powder or granules) can be dissolved in a liquid substance. Or, threads containing $EuD_4TEA$ can be spun and then woven into a fabric.

The following references, each of which is hereby incorporated herein by reference, are instructive regarding synthesis and fabrication of $EuD_4TEA$ and of articles and materials (e.g., polymeric or fibrous) that include $EuD_4TEA$: R. S. Fontenot, K. N. Bhat, W. A. Hollerman, and M. D. Aggarwal, "Europium Tetrakis Dibenzoylmethide Triethylammonium: Synthesis, Additives, and Applications," Chapter 7 (pages 147-235) in *Triboluminescence: Theory, Synthesis, and Application*, editors David O. Olawale, Okenwa O. I. Okoli, Ross S. Fontenot, and William A. Hollerman, Springer International Publishing, Cham, Switzerland (2016); Ross S. Fontenot, Stephen W. Allison, Kyle J. Lynch, William A. Hollerman, and Firouzeh Sabri, "Mechanical, Spectral, and Luminescence Properties of ZnS:Mn Doped PDMS," *Journal of Luminescence*, Volume 170, Part 1, pages 194-199, February 2016 (available online 27 Oct. 2015); Ross S. Fontenot, William A. Hollerman, Kamala N. Bhat, Mohan D. Aggarwal, and Benjamin G. Penn, "Incorporating Strongly Triboluminescent Europium Dibenzoylmethide Triethylammonium into Simple Polymers," *Polymer Journal*, Volume 46, pages 111-116, 2014 (published 18 Sep. 2013); U.S. Pat. No. 7,338,877 B1, August Karl Meyer et al., "Multicomponent Fiber Including a Luminescent Colorant," issued 4 Mar. 2008.

Also of interest with regard to the present invention are the following references, each of which is hereby incorporated herein by reference: William A. Hollerman, Ross S. Fontenot, Paul Darby, Nick Pugh, John Miller, "Using Exotic Materials Like Eud4tea and Mgd4tea to Monitor Damage and Radiation Exposure in Extreme Environments," *ECSarXiv*, The Electrochemical Society (ECS) (9 May 2018); W. A. Hollerman, R. S. Fontenot, S. Williams, and J. Miller, "Using Luminescent Materials as the Active Element for Radiation Sensors," *Proceedings SPIE* 9838, in *Sensors and Systems for Space Applications IX*, edited by K. D. Pham and G. Chen (SPIE, Baltimore, MD, USA, 19 Apr. 2016), 98380Z; Stephen A. Williams, *Half-Brightness Measurements of Candidate Radiation Sensors*, Master's Thesis, a Thesis Presented to the Graduate Faculty of the University of Louisiana at Lafayette in Partial Fulfillment of the Requirements for the Degree Master of Science, University of Louisiana at Lafayette, Summer 2016, published by ProQuest LLC, publication number 10163329 (2016).

Exemplary inventive practice is based in part on the phenomenon, discovered and studied by the present inventors, that when EuD$_4$TEA is exposed to charged particles such as protons, a bright red light becomes visible that is indicative of the radiation. The gammas rays produced during such an interaction will not produce light. For instance, a health physicist can incorporate EuD$_4$TEA inside a specimen to visually see his proton or carbon beam. The health physicist can thus fine-tune an ion beam—e.g., a proton beam or a carbon beam—for difficult cancer locations. The inventive methodology can be practiced not only to see proton beams but to see any and all types of particle beams. Exemplary inventive practice provides for use of EuD$_4$TEA as the sole luminescent (e.g., radioluminescent or photoluminescent) substance. Nevertheless, some inventive embodiments provide for use of other luminescent materials, such as manganese-doped zinc sulfide nanoparticles (ZnS:Mn), either instead of or in addition to EuD$_4$TEA.

The inventive sensor apparatus as exemplarily embodied provides a visual indication—e.g., a bright red light—that ionizing radiation is present at a particular location. Emphasized in the instant disclosure are medical (e.g., oncological) applications of the present invention. According to exemplary medical embodiments of the present invention, a material that includes EuD$_4$TEA is implemented to achieve more precise directing or imaging, and hence more precise radiotherapy, of cancerous tumors. For instance, in administering proton therapy, an inventive practitioner sees only the beam of protons. That is, the inventive practitioner sees the beam of protons but does not see gammas that could also be produced during the reaction, thereby allowing the inventive practitioner to fine-tune his/her beam to direct the proton radiation at a particular spot.

Since inventive practice is efficacious at destroying living tissue, medical applications such as involving cardiac ablation (e.g., to cure heart arrhythmia, such as atrial fibrillation) and orthopedic surgery are also possible. Although medical applications of the present invention are emphasized in the instant disclosure, it is appreciated by the skilled artisan who reads the instant disclosure that the present invention admits of multifarious non-medical applications. For instance, in inventive applications involving security, a bright red luminescence (radioluminescence or photoluminescence) emanating from an inventive sensor can serve as a warning, alerting personnel as to a hazardous presence of ionizing radiation.

Figure 4:
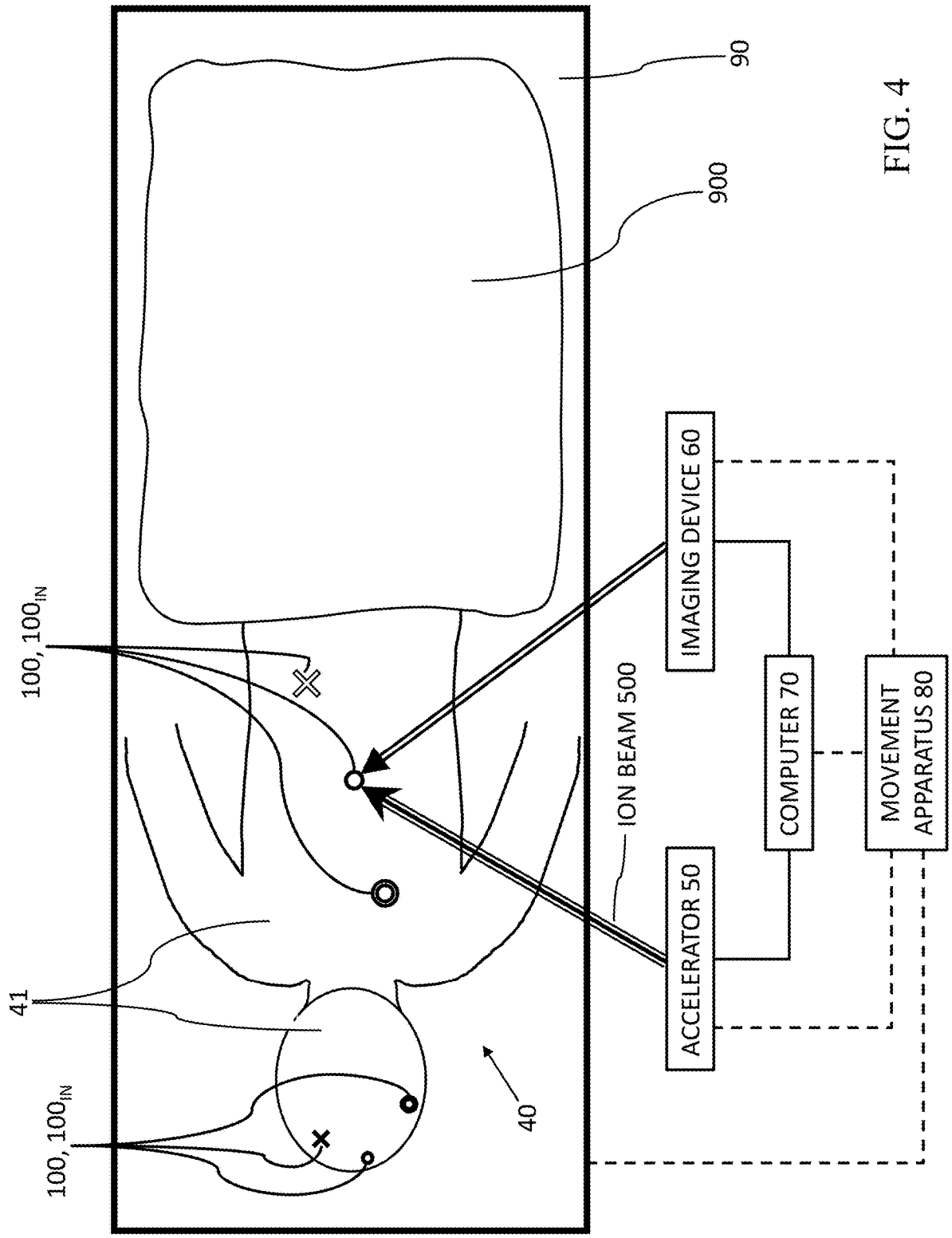
FIG. 4 is a top plan view of an embodiment of a human patient situated on a treatment couch to receive ion beam therapy in accordance with the present invention. In this example of inventive practice, EuD$_4$TEA-inclusive markers are attached to the patient's skin on the patient's head and trunk. The markers shown in FIG. 4 and FIG. 5 serve to facilitate aiming of the ion beam, in furtherance of precise impingement of the ion beam with respect to the targeted cancerous tissue.
Figure 5:
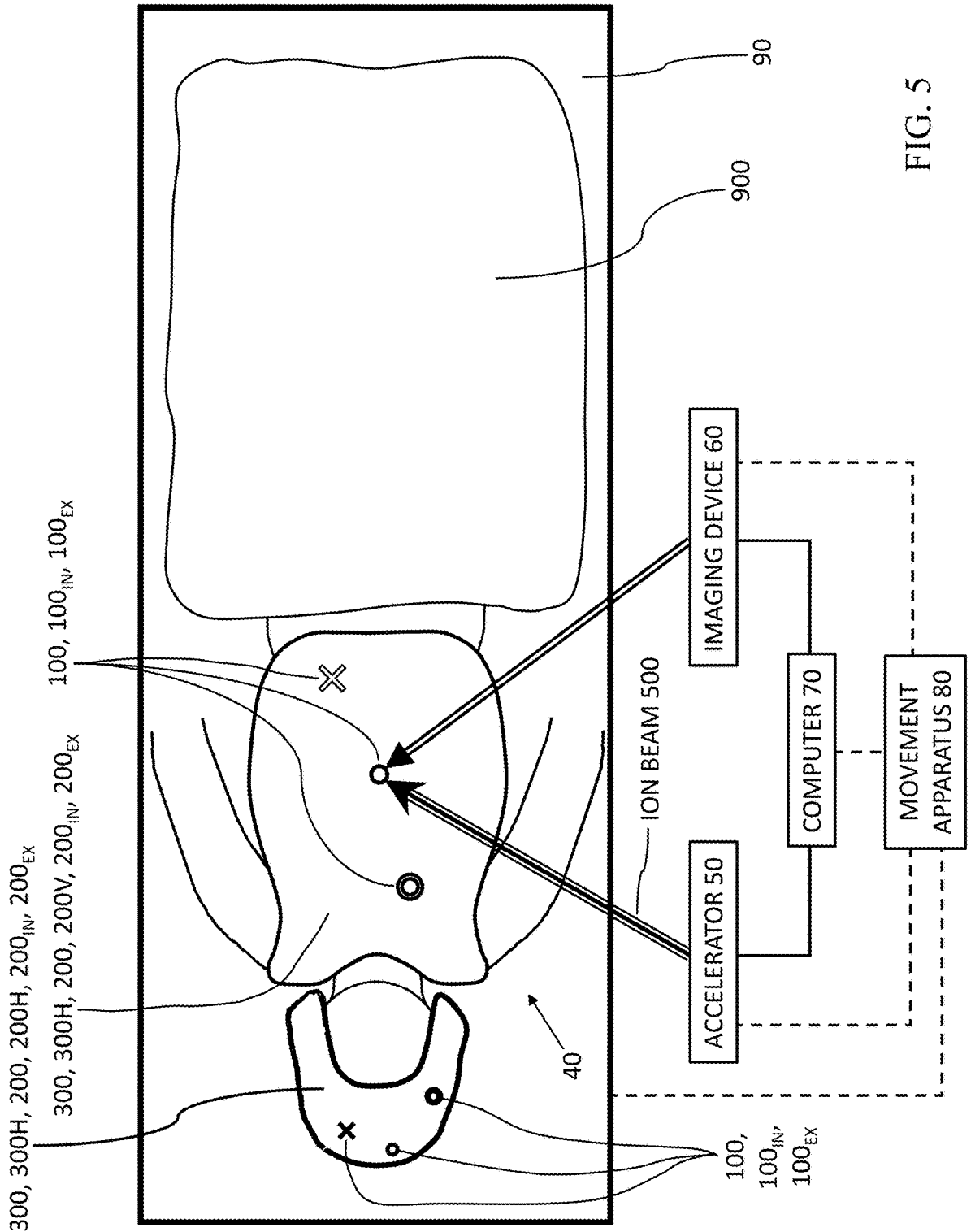
FIG. 5 is a top plan view, similar to the view of FIG. 4, of a human patient situated on a treatment couch to receive ion beam therapy in accordance with a different embodiment of the present invention. In this example of inventive practice, the patient is fitted with two inventive EuD$_4$TEA-inclusive coverings, viz., an inventive head covering (e.g., hat or helmet) and an inventive torso covering (e.g., a vest or apron), each inventive covering including markers.

With reference to FIGS. 4 and 5, a human patient 40 beset with malignancies lies on a movable treatment couch 90 to receive external ion beam radiation therapy. Particle accelerator 50 (e.g., proton accelerator, ion accelerator, linear accelerator, cyclotron, or synchrotron) emits an ion beam 500 (e.g., proton beam or carbon beam) that is aimed to impinge upon marker devices 100, one marker device 100 at a time. Inventive marker devices 100 are situated on patient 40 at selected locations. The markers 100 are utilized by inventive practitioners (who are, for instance, health physicists or nuclear physicists) to visually perceive and align their ion beams for multifarious medical and non-medical applications. Digital imaging device 60 (e.g., a device including a camera, image sensor, or photodetector) images the locations of impingement of ion beam 500 upon patient 40's skin 41, thus capturing each point of luminescent impingement of ion beam 500 upon a marker 100. Every time that ion beam 500 impinges upon EuD$_4$TEA that is contained in a marker 100, that point of impingement luminesces a bright red light. Imaging device 60 focuses upon these manifestations of luminescence.

Exemplary inventive practice implements a computer 70, along with a computer display and one or more peripheral devices, to facilitate inventive practice of ion beam treatment. Computer 70 includes a processor and memory/storage, both volatile and non-volatile, and is connected to particle accelerator 50, imaging device 60, and equipment movement apparatus 80. According to exemplary inventive embodiments, computer 70 acts as a processor-controller to control and receive signals or data from accelerator 50, imaging device 60, and movement apparatus 80. The term "movement apparatus," as used herein in the context of inventive practice, broadly refers to any of various mechanical and electro-mechanical devices that are known in the pertinent arts and that may be used to impart movability to accelerator 50, imaging device 60, and/or treatment couch 90.

For instance, movement apparatus 80 may include a medical gantry, which houses or support accelerator 50 and provides movability for accelerator 50. The medical gantry may include a mechanism that encircles treatment couch 90 about the longitudinal axis of couch 90, with the patient 40 lying upon couch 90 in a longitudinal-axial direction. The gantry may serve to adjust the position of accelerator 50 both lengthwise along, and circumferentially around, couch 90's axis. As other examples, movement apparatus 80 may include devices as gantries, cranes, tripods, dollies, etc., to provide movability for imaging device 60 or for treatment couch 90. Accelerator 50 and/or imaging device 60 and/or treatment couch 90 may be attributed with movability in six degrees of freedom. Inventive practice may provide for utilization of a conventional treatment couch that is electro-mechanically attributed with six degrees of freedom, e.g., up-and-down, sideways, and longitudinal-axial movability.

According to some inventive embodiments, movement apparatus 80 represents a unit that is capable of imparting synchronous and/or separate movability to accelerator 50, imaging device 60, and couch 90. An ordinarily skilled artisan who reads the instant disclosure will be familiar with known systems and methods, in general, for selectively moving and configuring radiation delivery and/or luminescence-related imaging and/or patient reclining, in the context of administering radiation therapy in accordance with the present invention.

Computer 70 has algorithmic software, resident in its memory, for controlling activation/inactivation, radiation transmission, movement, and positioning of accelerator 50 and/or imaging device 60 and/or treatment couch 90. Of particular note, according to exemplary inventive practice, computer 70 controls delivery and intensity of ion beam 500 with respect to patient 40. Patient 40 may be male or female, and may be a human or a dog or other animal, in keeping with the principles of the present invention. Hence, skin 41 may be human skin or animal skin, depending on the nature of the patient 40. Each marker 100 is implemented whereby an ion beam 500 is aimed at and passes through the marker 100 and a portion of the human 40 so that ion beam 500 precisely impinges upon the cancerous tumor 1000 that is located below the marker 100 and interior to the human 40. Otherwise expressed, ion beam 500 refracts through marker 100 and hits the malignant target 1000.

As shown in FIG. 4, patient 40 is wearing no clothing above his waist, his head is shaved, and he has six markers 100 placed (e.g., adhered) directly on his skin, viz., three markers 100 on his head and three markers 100 on his torso. According to exemplary inventive practice, each marker 100 is an EuD$_4$TEA-inclusive marker $100_{IN}$, and is situated at a different location on patient 40's skin 41. Depending on the inventive embodiment, markers $100_{IN}$ may be embodied, for instance, as a patch, sticker, applique, gel, marking, etc., and may be transparent, translucent, or opaque. Patient 40's lower body is covered by a radiation-protective (e.g., lead) shield 800. Each $EuD_4TEA$-inclusive marker $100_{IN}$ is made so that $EuD_4TEA$ material is incorporated therein.

According to some inventive embodiments, at least one $EuD_4TEA$-inclusive marker $100_{IN}$ is embodied as a solid structure. According to other inventive embodiments, at least one $EuD_4TEA$-inclusive marker $100_{IN}$ is embodied as a gel (e.g., a gelatin or other type of gelatinous or mesophase substance), which may be applied to human skin 41. As another example, inventive practice is possible whereby an $EuD_4TEA$-exclusive marker $100_{EX}$ and an $EuD_4TEA$-inclusive marker $100_{IN}$ are collocated atop human skin 41. Exemplary inventive practice involving direct association of $EuD_4TEA$-inclusive markers $100_{IN}$ to skin 41 implements each $EuD_4TEA$-inclusive marker $100_{IN}$ either alone or in collocational combination with an $EuD_4TEA$-exclusive marker $100_{EX}$.

As correspondingly shown in FIG. 4 and FIG. 5, six markers 100 are placed upon the skin 41 of patient 40 at various locations of the head and upper body, and a radiation-protective (e.g., lead) shield 800 is used to cover the lower body. According to inventive practice exemplified by either FIG. 4 or FIG. 5, marker 100 may be variously embodied, depending on the inventive embodiment; for instance, marker 100 may be a patch, sticker, applique, gel, marking, etc., and may be transparent, translucent, or opaque. Similarly, depending on the inventive embodiment, covering device 300 may be transparent, translucent, or opaque.

In contrast to the hatless, shirtless patient 40 shown in FIG. 4, the patient 40 shown in FIG. 5 is wearing two covering devices 300, viz., a head covering (e.g., hat, cap, or helmet) 300H and a torso covering (e.g., vest or other garment) 300V. Head covering 300H may be, for instance, a skullcap or closely fitted hat. As distinguished from FIG. 4, FIG. 5 depicts three markers 100 placed on head covering 300H and three markers 100 placed on torso covering 300V. Each inventive covering 300 includes two components, viz., at least one marker 100 and a covering form 200. As used herein in the context of inventive practice, the term "covering form" refers to the basic structure or structural framework 200 of a covering 300.

Figure 6:
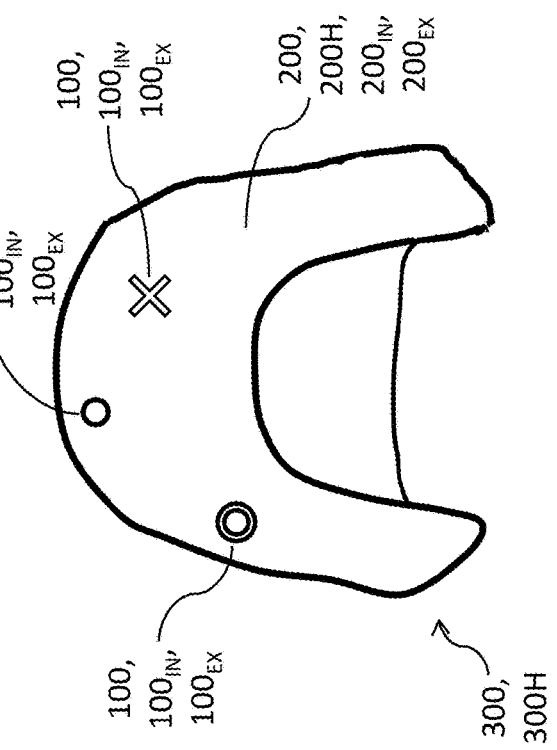
FIG. 6 is an elevation view of an embodiment of an inventive $EuD_4TEA$-inclusive head covering such as that shown in FIG. 5.
Figure 7:
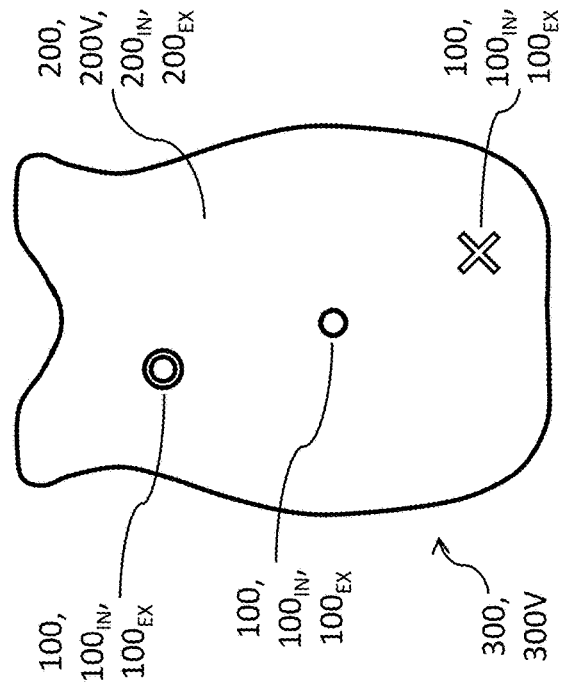
FIG. 7 is an elevation view of an embodiment of an inventive $EuD_4TEA$-inclusive torso covering such as that shown in FIG. 5.

In the inventive example shown in FIG. 6, inventive head covering 300H includes a head covering form 200H and three markers 100. In the inventive example shown in FIG. 7, inventive torso covering 300V includes a torso covering form 200V and three markers 100. According to exemplary inventive practice, a covering form 200 is made of a plastic or composite or other solid material (e.g., a transparent polymeric material) and defines the three-dimensional geometric shape of inventive covering 300, thus constituting the major structural component of inventive covering 300. In essence, covering form 200 represents the predominant structural mass and shape of inventive covering 100, unenhanced by one or more markers 100. Hence, hat form 200H is essentially inventive hat 300, but without any markers 100 associated therewith. Similarly, vest form 200V is essentially inventive vest 300, but without any markers 100 associated therewith.

In exemplary practice of the present invention, a given marker 100 may be embodied as either an $EuD_4TEA$-inclusive marker $100_{IN}$ or an $EuD_4TEA$-exclusive marker $100_{EX}$. When a marker 100 is implemented so as to affix directly to human skin 41, the marker 100 will generally be embodied as an $EuD_4TEA$-inclusive marker $100_{IN}$. In contradistinction, when a marker 100 is implemented as part of an inventive covering 300 such as head covering 300H or torso covering 300V, the marker 100 may be embodied as either an $EuD_4TEA$-inclusive marker $100_{IN}$ or an $EuD_4TEA$-exclusive marker $100_{EX}$. The characteristic of a marker 100 as either an $EuD_4TEA$-inclusive marker $100_{IN}$ or an $EuD_4TEA$-exclusive marker $100_{EX}$ may depend on the characteristic of its associated covering 300 as either an $EuD_4TEA$-inclusive covering $300_{IN}$ or an $EuD_4TEA$-exclusive covering $300_{EX}$.

Some inventive embodiments provide for one or more $EuD_4TEA$-exclusive markers $100_{IN}$ in association with an $EuD_4TEA$-inclusive covering form $200_{IN}$. Some other inventive embodiments provide for one or more $EuD_4TEA$-inclusive markers $100_{IN}$ in association with an $EuD_4TEA$-exclusive covering form $200_{IN}$. According to exemplary inventive practice, the contrastive distinction in terms of $EuD_4TEA$-containment and $EuD_4TEA$-noncontainment serves to facilitate the inventive practitioner's effort to aim ion beam 500 with pinpoint accuracy in the direction of the targeted tumor 1000. According to some inventive embodiments, the visual contrast between an $EuD_4TEA$-inclusive marker $100_{IN}$ and human skin 40 will similarly assist the inventive practitioner in directing the ion beam 500.

Exemplary inventive practice involves use of at least one $EuD_4TEA$-inclusive device which, depending on the inventive embodiment, includes at least one $EuD_4TEA$-inclusive marker $100_{IN}$ and/or at least one $EuD_4TEA$-exclusive marker $100_{EX}$. An inventive $EuD_4TEA$-inclusive device may be embodied, for instance, primarily as an $EuD_4TEA$-inclusive marker $100_{IN}$, or primarily as an $EuD_4TEA$-inclusive covering 300. An inventive $EuD_4TEA$-inclusive covering 300 may be embodied as an $EuD_4TEA$-inclusive head covering 300H or as an $EuD_4TEA$-inclusive body (e.g., torso) covering 300V. An $EuD_4TEA$-inclusive head covering 300H may be, e.g., a kind of hat, cap, or helmet. An $EuD_4TEA$-inclusive body covering 300V may be, e.g., a kind of vest, smock, apron, cast, or sleeve, serving to cover, e.g., an arm, a leg, the torso, or one or more areas thereof.

Figure 8:
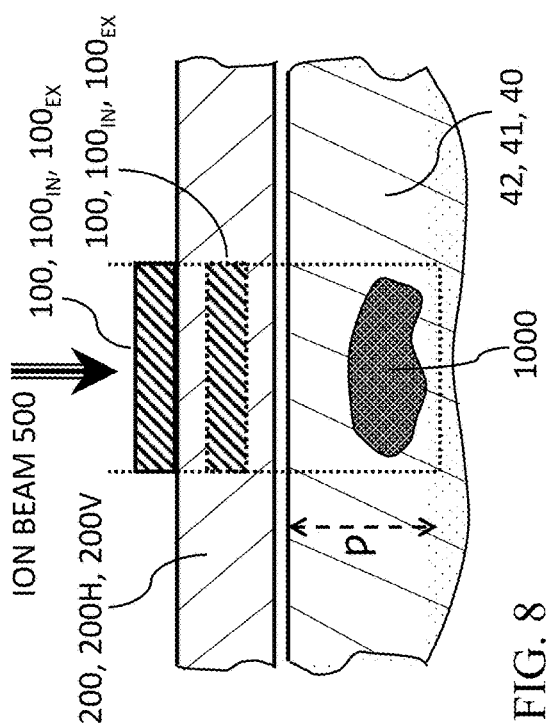
FIGS. 8 and 9 are cross-sectional views illustrative of association of an inventive marker with an inventive $EuD_4TEA$-inclusive covering and/or with human skin.
Figure 9:
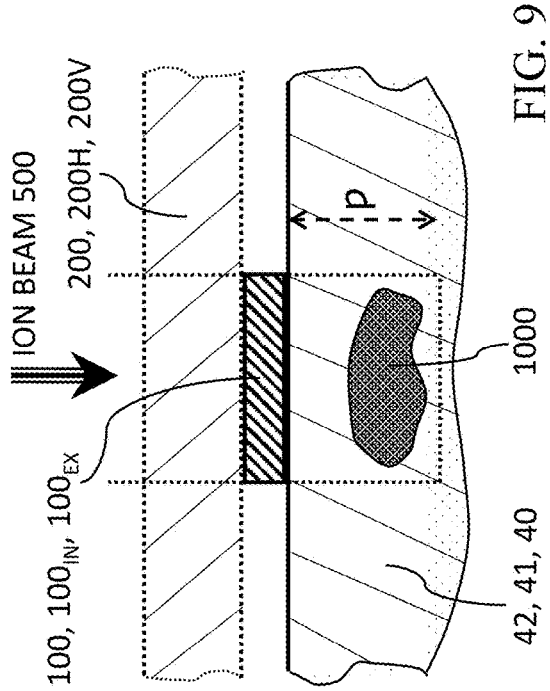

FIGS. 8, 9, and 11 through 15 illustrate the positioning of a marker 100 in super-positional relationship and in co-extensive and/or super-extensive relationship, with respect to a targeted tumor 1000 inside the head or body of a human 40. According to the view of FIGS. 8, 9, and 11 through 15, tumors 1000 are understood to be located in or below the skin 41 (e.g., in body organ or tissue 42) and to be seen in see-through fashion. Tumor 1000 is characterized by a tumor border 1001. According to exemplary inventive practice, the target zone 31 of inventive marker 100 extends to or beyond the perimeter of tumor 1000, so that the visible luminescence of an ion beam 500 passing through inventive marker 100 completely encompasses tumor 1000. Otherwise expressed, target zone 31 is at least coextensive with tumor 1000, wherein target zone delineation 33 circumscribes or surrounds tumor border 1001. Ion beam 500 passes through the entire area of target zone 31, thereby entirely enveloping the tumor 1000 situate beneath target zone 31. For instance, in completely encompassing tumor 1000, ion beam 500 may extend slightly or somewhat beyond tumor 1000 so as to be proximate the side surfaces and far end surfaces of tumor 1000, such as shown in FIGS. 8 and 9.

As depicted in FIGS. 4 through 7 and 11 through 15, an inventive marker 100 can have any of a variety of shapes, sizes, and compositions. Markers 100 may be constituted as solid coverings having selected physical characteristics, such as small patches applicable at selected locations anywhere on the human body. A solid $EuD_4TEA$-inclusive marker 100 may be "self-marked," for instance by an $EuD_4TEA$-exclusive marking (e.g., an "X" or an "O") thereupon. Conversely, a solid $EuD_4TEA$-exclusive marker 100 may be "self-marked," for instance by an $EuD_4TEA$-inclusive marking thereupon. Whether $EuD_4TEA$-inclusive or $EuD_4TEA$-exclusive, a marker 100 may be devised to have practically any shape, including but not limited to curved, straight, rectilinear, curvilinear, polygonal (e.g., triangular, rectangular, pentagonal, hexagonal, etc.), cylindrical, annular, "X"-shaped, "O"-shaped, round (e.g., circular, oval, elliptical, etc.), or some combination thereof.

An ion beam 500 that is directed toward the area of an $EuD_4TEA$-inclusive marker 100 that is placed on human skin 41 will yield visible light only when ion beam 500 impinges upon the $EuD_4TEA$-inclusive marker 100 itself, the entire $EuD_4TEA$-inclusive marker 100 thus luminescing. The ion beam is transmitted through the marker and a portion of the human head or body, finally hitting the malignant target inside the human head or body. According to some inventive embodiments, a gel marker 100 is applied as a small spot on skin 41 with pinpoint accuracy. An ion beam 500 may be directed to the entirety of a gel spot marker 100, which is configured in size and shape to encompass the entire area of a malignancy 1000.

Figure 12:
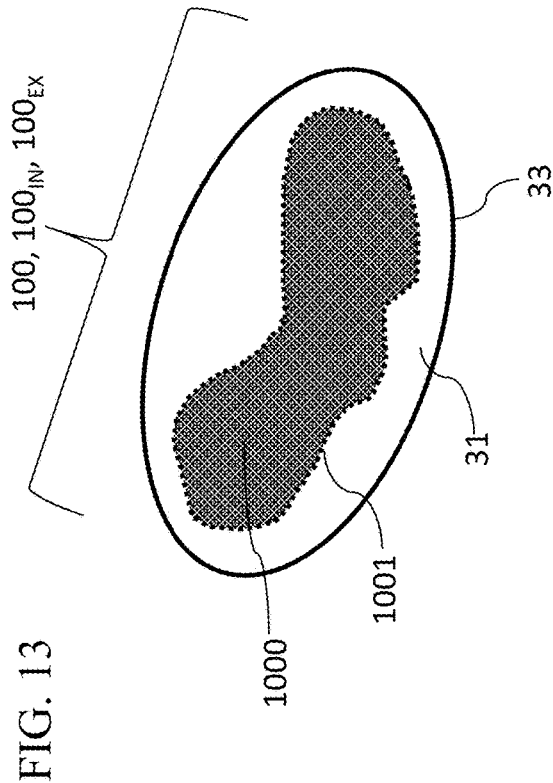
Figure 13:
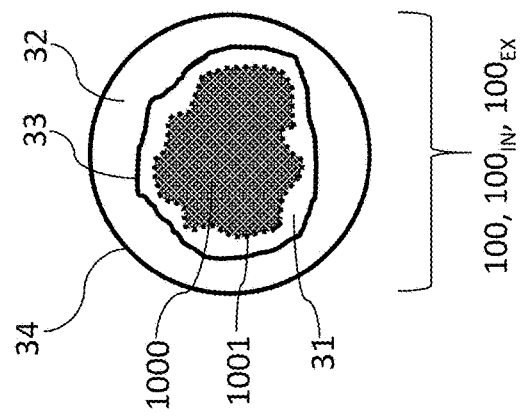
Figure 14:
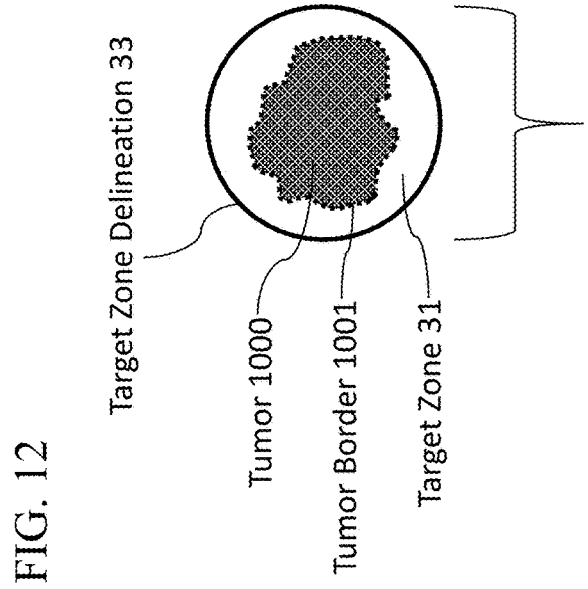

As exemplarily embodied, an inventive marker 100 has an outer perimeter, referred to herein as either a target zone delineation 33 or a vicinity zone delineation 34, depending upon the inventive embodiment. If, for example, marker 100 is configured as completely $EuD_4TEA$-inclusive, such as shown in FIGS. 12 through 14, the outer perimeter of marker 100 is target zone delineation 33. According to such inventive embodiments, marker 100 has a target zone 31 but does not have a vicinity zone 32.

Figure 11:
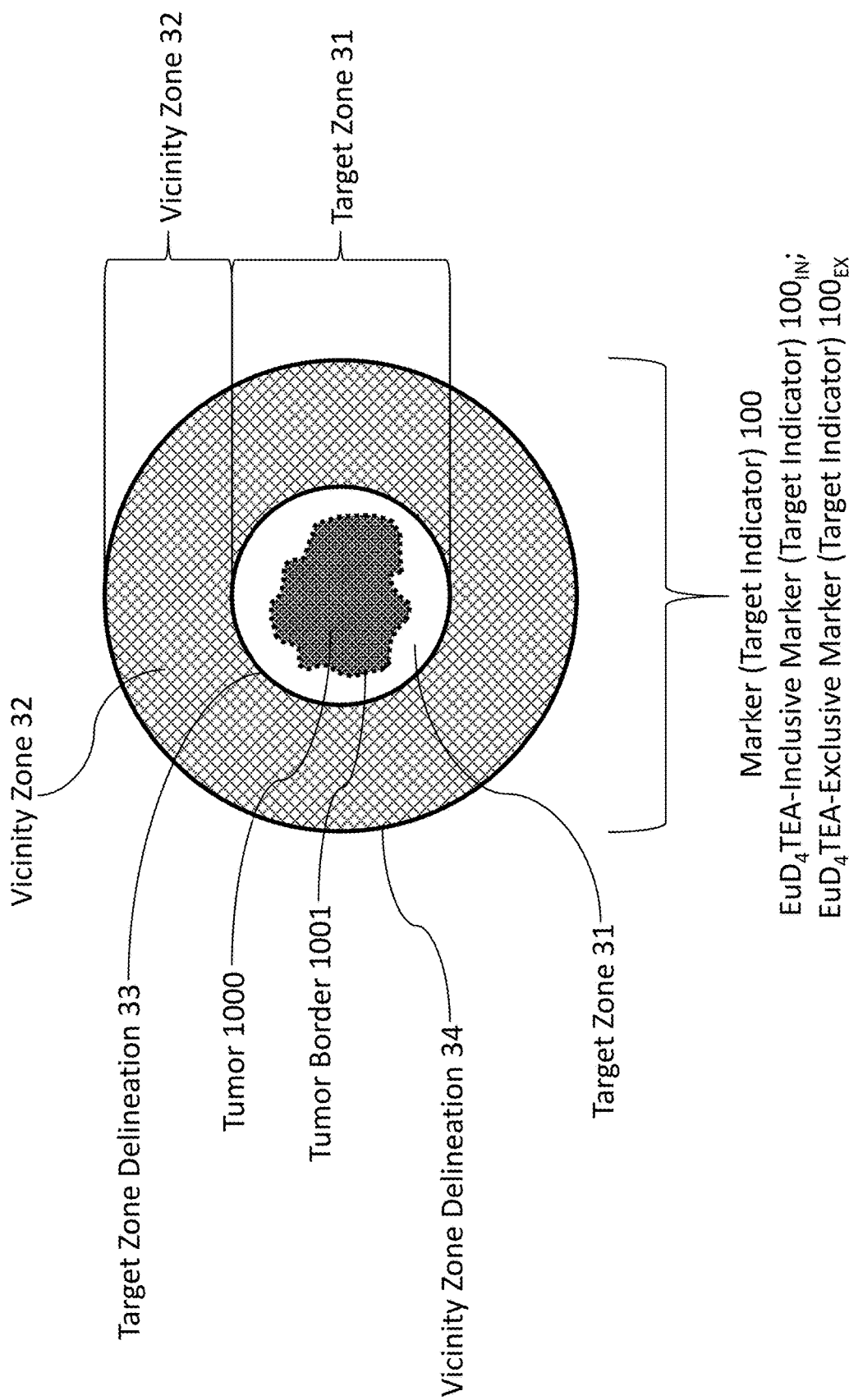
FIGS. 11 through 15 are diagrammatic representations of variously configured pairings of inventive markers and cancerous tumors, in accordance with the present invention. Depicted in each of FIGS. 11 through 15 is an inventive marker and a cancerous tumor located on or beneath the patient's skin. The inventive marker is above and geometrically aligned with the tumor. As perceived in an approximately normal direction through the inventive marker, the cancerous tumor is either at or below the skin surface and lies completely within the target zone of the marker.
Figure 15:
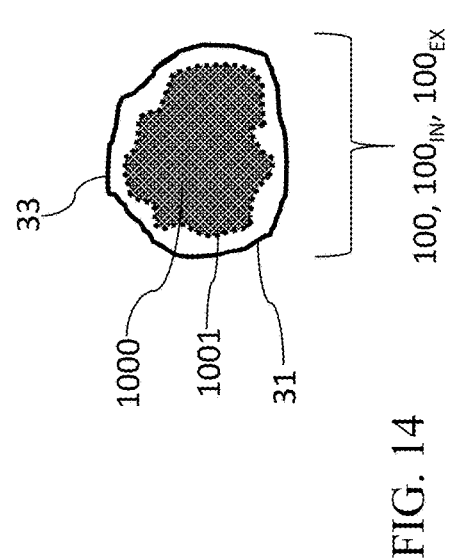

According to some embodiments of the present invention, a marker 100 is characterized by a target zone 31 and a vicinity zone 32. As illustrated in FIGS. 11 and 15, a target zone delineation 33 delimits a target zone 31, and a vicinity zone delineation 34 delimits a vicinity zone 32. For instance, it may be considered that in a two-zone marker 100, target zone 31 represents an $EuD_4TEA$-inclusive central area of marker 100, and vicinity zone 32 represents an $EuD_4TEA$-exclusive peripheral area of marker 100; marker 100 is configured as having an $EuD_4TEA$-inclusive central region 31 and an $EuD_4TEA$-exclusive peripheral region 31. Alternatively, it may be considered that in a two-zone marker 100, target zone 31 represents an $EuD_4TEA$-exclusive central area of marker 100, and vicinity zone 32 represents an $EuD_4TEA$-inclusive peripheral area of marker 100; marker 100 is configured as having an $EuD_4TEA$-exclusive central region 31 and an $EuD_4TEA$-inclusive peripheral region 31.

By way of example, a continuous $EuD_4TEA$-inclusive gelatinous marker 100 may be collocated beneath a toroidal or annular $EuD_4TEA$-exclusive solid marker 100. The exterior marker 100 does not contain any $EuD_4TEA$. According to this combination of an outer annular solid $EuD_4TEA$-exclusive marker 100 component and an inner gelatinous $EuD_4TEA$-inclusive marker 100 component that is round or oval or irregularly shaped. Ion beam 500 is aimed at the $EuD_4TEA$-inclusive interior gelatinous marker 100 component, which is deposited on human skin 41 in circumscriptive geometric relationship to tumor 1000.

As another inventive example, a continuous $EuD_4TEA$-exclusive solid marker 100 may be collocated atop and surrounded by a continuous $EuD_4TEA$-inclusive gelatinous marker 100 deposited on human skin 41. According to this combination of an inner solid $EuD_4TEA$-exclusive component and an outer gelatinous $EuD_4TEA$-inclusive component, ion beam 500 may be aimed at the $EuD_4TEA$-exclusive solid centroid component encompassing tumor 1000, somewhat in a manner of hitting a non-luminescent bullseye encircled by a luminescent ring.

By way of further inventive example, a transparent gelatinous $EuD_4TEA$-inclusive material may be placed on a larger area encompassing the smaller area of the malignancy. The target area is within and a subset of the entire gel-covered area. A marking (e.g., an "X" or an "O") is placed on the skin underneath the $EuD_4TEA$-inclusive gel at the precise target location. The beam remains visible in the gel-covered area and is directed by the inventive practitioner to "hit the spot", i.e., the marked target (e.g., an "X" or an "O"). The direction of the beam-induced luminescence is adjusted until it hits the spot, e.g., the center of the X-marking or the O-marking. Human skin (or animal skin) may be marked immediately beneath a transparent $EuD_4TEA$-inclusive gel. For instance, $EuD_4TEA$-inclusive gelatinous marker 100 may be applied directly to human skin 41 (e.g., directly deposited as a thin layer on human skin 41) and directly over an $EuD_4TEA$-exclusive graphic-marking marker 100 (such as an "X" or an "O"), which for instance may be drawn upon or adhered to a small area of human skin 41.

FIG. 10 conveys in a tabular presentation that, according to numerous variations of exemplary inventive practice, marker 1000 may be: $EuD_4TEA$-inclusive or $EuD_4TEA$-exclusive; embodied as a solid marker 1000 or a gelatinous marker 1000; and implemented in direct association with a patient 40's skin 41 or in combination with a covering form 200. A covering form 200 may be an $EuD_4TEA$-inclusive covering form 200 or an $EuD_4TEA$-exclusive covering form 200. Similarly, a medical phantom form 250 may be an $EuD_4TEA$-inclusive medical phantom form 250 or an $EuD_4TEA$-exclusive medical phantom form 250. According to usual inventive practice of inventive medical phantoms 350, medical phantom form 250 is transparent so that the luminescent light is visible all the way through the medical phantom form 250 until reaching the site of the facsimile tumor 1000.

Inventive practice may involve use of an $EuD_4TEA$-exclusive marker 1000 in contrastive combination with an $EuD_4TEA$-inclusive marker 1000, or with an $EuD_4TEA$-inclusive covering form 200, or with an $EuD_4TEA$-inclusive phantom form 250. However, as indicated in FIG. 10, inventive practice will usually not involve use of an $EuD_4TEA$-exclusive marker 1000 in such a way that there is no proximate $EuD_4TEA$-inclusive material to afford contrastive visibility or discernment to the $EuD_4TEA$-exclusive marker 100. Similarly, inventive practice will usually not involve use of an $EuD_4TEA$-inclusive marker 100 in such a way that there is no proximate $EuD_4TEA$-exclusive material to afford contrastive visibility or discernment to the $EuD_4TEA$-inclusive marker 1000.

A solid covering form 200 may be transparent or non-transparent (e.g., translucent or opaque), and may be rigid (e.g., firm) or flexible (e.g., resilient or elastic). According to usual inventive practice, a transparent solid phantom form 250 is transparent and may be rigid or flexible. An example of a solid covering form 200 is a structure made of a solid plastic containing $EuD_4TEA$ that is, for instance, uniformly distributed throughout the structure. As further examples, nontransparent solid covering form 200 may be a nontransparent solid $EuD_4TEA$-containing plastic or a garment made of $EuD_4TEA$-containing threads (e.g., wherein the threads are uniformly distributed throughout the fabric or cloth of the garment). An $EuD_4TEA$-inclusive or $EuD_4TEA$-exclusive marker 100 structure may be configured as a hat, cap, or helmet for covering at least a portion of the head, or as a vest, shirt, or shield for covering at least a portion of the torso, or as a wrapping, bracelet, or brace for covering at least a portion of an arm or a leg. Generally speaking, many malignancies are found in the head and/or torso, where major tissue and organs are located.

An $EuD_4TEA$-inclusive marker 100 (e.g., structure or gel) may be situated above a malignant target region so as to be co-extensive and/or super-extensive with respect to the malignant target region. The beam 500 is visible only when it hits the malignancy 1000; when the beam 500 does not hit the malignancy 1000, the beam 500 is not visible. If marker 100 is strictly co-extensive with respect to malignancy 1000, the entire luminescence of the beam corresponds to the entire malignant area. If marker 100 is at least partly super-extensive with respect to malignancy 1000, beam 500 is visible not only in the malignant area 1000 but also in the vicinity of the malignant area 1000. Ion beam 500 may be precisely aimed at a malignant point in a manner akin to adjusting the direction of a rangefinder or rifle using a laser beam to indicate where a laser beam hits a target point.

Figures 16, 17:
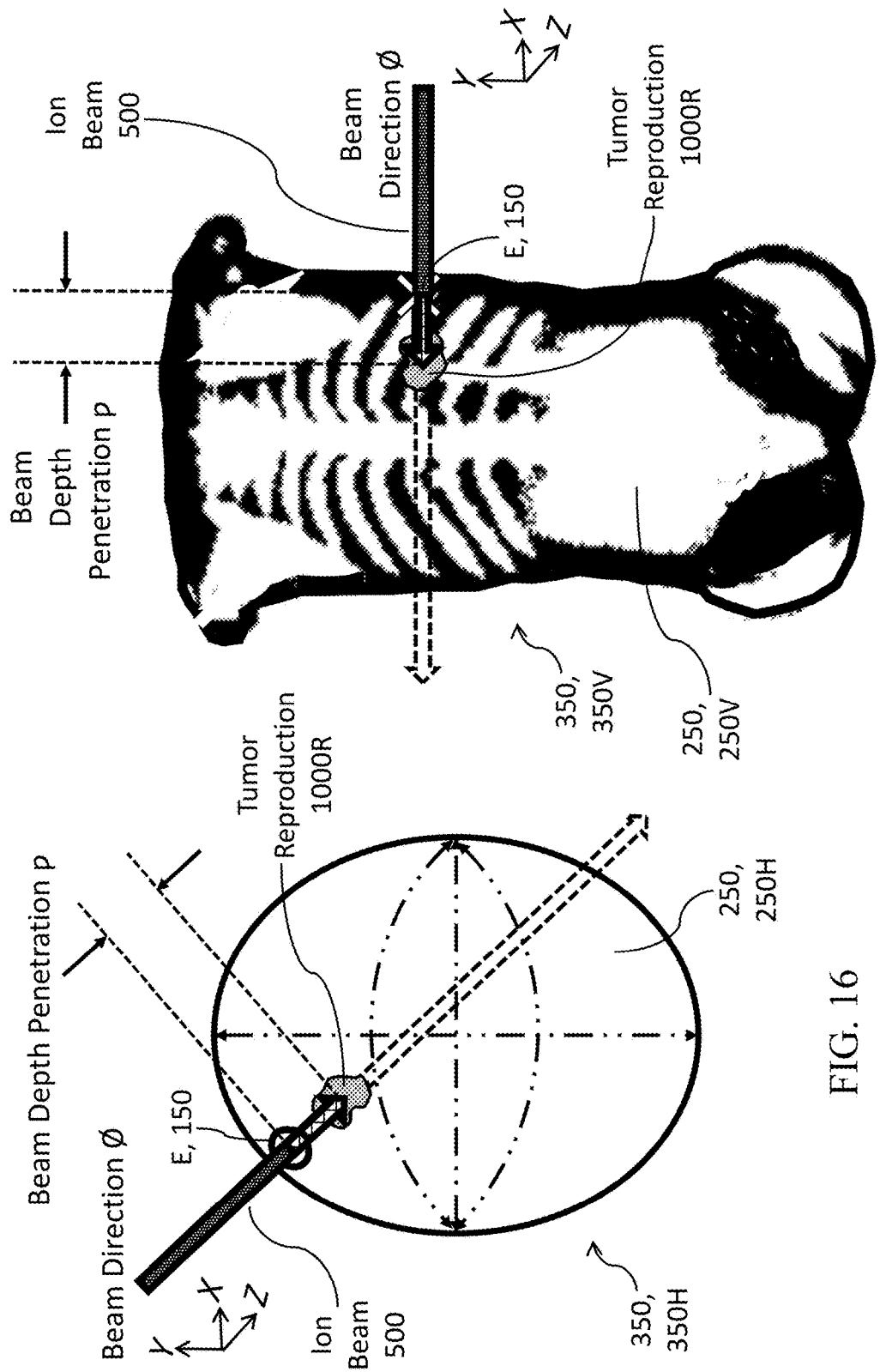
FIGS. 16 and 17 are diagrammatic representations of two different embodiments of $EuD_4TEA$-inclusive medical phantoms in accordance with the present invention. The inventive phantom depicted in each drawing contains $EuD_4TEA$ and simulates a human head (FIG. 16) or human torso (FIG. 17) that is beset with one or more cancerous tumors. An exemplary medical phantom in accordance with the present invention contains $EuD_4TEA$ material and one or more facsimile tumors with respect to a real patient. The $EuD_4TEA$ material luminesces when interacting with an ion beam. An inventive practitioner performs ion beam testing on the medical phantom to determine optimal parameters for the ensuing ion beam delivery to the real patient.

FIGS. 16 and 17 illustrate, by way of example of inventive practice, two different inventive embodiments of a medical phantom 350, which includes a medical phantom form 250 and at least one tumor reproduction 1000R located in the interior of medical phantom 350. Medical phantom form 250 is a replica of a person or portion of a person, e.g., a person's head or body or body part. FIG. 16 depicts an inventive human head phantom 350H having phantom head form 250H and tumor reproduction 1000R. FIG. 17 depicts an inventive human torso phantom 350V having phantom torso form 250V and tumor reproduction 1000R. The three-dimensional phantom form 250 may include three-dimensional representations of anatomical features such as ribs, scapulae, and clavicles. Phantom form 250 and tumor reproduction 1000R serve to simulate or duplicate, to scale, the actual human or human part and the tumor situate therein of the patient being treated.

A phantom form 250 may be made of, for instance, a solid polymeric (e.g., plastic) material or a composite material. An inventive medical phantom 350 can be fabricated, for example, whereby some $EuD_4TEA$ is incorporated (e.g. doped) into PDMS (polydimethylsiloxane). An inventive phantom form 250 includes $EuD_4TEA$ but does not include any tumor reproduction 1000R. The $EuD_4TEA$-containing PDMS medical phantoms 350 may be molded or casted, for instance, as duplicating real-life shapes of human or animal patients. In the fabrication process, the tumor replica(s) 1000R is/are placed inside phantom 350 with requisite precision in correspondence to the locations of the actual tumor(s) 1000 inside person 40.

In accordance with frequent practice of the present invention, inventive practice of covering form 200 and inventive practice of phantom form 250 may involve selection of same or similar materials. Like an exemplary transparent solid covering form 200, an exemplary transparent solid phantom form 250 is a structure made of a transparent solid plastic containing $EuD_4TEA$ uniformly throughout the structure. An inventive medical phantom 350 may represent practically any transparent solid device of selected size and shape and selected firmness/rigidity or flexibility. For instance, a transparent $EuD_4TEA$-containing phantom 250 structure can be configured as a head or a torso.

According to exemplary inventive practice involving inventive one or more inventive medical phantoms 350, a simulation of radiation delivery using an inventive phantom 350 is performed in order to plan a subsequent actual delivery of the radiation. Plural inventive simulations may be performed in order to plan plural inventive deliveries of radiation. For example, an inventive medical phantom 350 may be situated on a treatment couch 90 precisely where the patient 40 or corresponding portion thereof will subsequently be situated. The medical physicist or radiologist can adjust ion beam 500 with respect to the geometric and radiative characteristics of the ion beam.

For instance, the direction and intensity of a beam may be adjusted in accordance with the visibility of the beam in the three-dimensional space within the phantom structure. The brighter is the luminescence (red light), the more intense is the beam. It is desirable to concentrate the most intense ion radiation on the malignancy. The most intense beams can be adjusted in strength and direction to maximize radiation delivery in comportment with the exact locations of the malignancies in the three-dimensional space inside the phantom.

In terms of visual contrast between $EuD_4TEA$-inclusive material and $EuD_4TEA$-exclusive material, there are at least two $EuD_4TEA$-related modes of inventive practice involving a medical phantom 350. According to a first mode of inventive phantom practice, phantom form 250 is transparent and $EuD_4TEA$-inclusive, and interior tumor reproduction 100R is $EuD_4TEA$-exclusive (and may be either transparent or non-transparent). $EuD_4TEA$-exclusive tumor reproduction 1000R is contained in an $EuD_4TEA$-inclusive matrix, viz., $EuD_4TEA$-inclusive phantom form 250. According to a second mode of inventive phantom practice, phantom form 250 is transparent and $EuD_4TEA$-exclusive, and interior tumor reproduction 100R is transparent and $EuD_4TEA$-inclusive. $EuD_4TEA$-inclusive tumor reproduction 1000R is contained in an $EuD_4TEA$-exclusive matrix, viz., $EuD_4TEA$-exclusive phantom form 250.

The present invention's first mode of phantom structure is often a preferable mode of practice. According to exemplary inventive practice of the first phantom mode, the transmission of ion beam 500 is directed linearly through the interior of phantom 350, with tumor reproduction 1000R in the direct path of ion beam 500. The geometric path of the ion beam 500 continues in a straight line commencing from accelerator 50 and proceeding through and beyond the inventive phantom 350. While traveling through a portion of the interior of phantom form 250, ion beam 500 is visible until reaching tumor reproduction (replica) 1000R. Ion beam 500 appears as a "beacon" of visible light inside phantom form 250, thereby conveying where the ion particle radiation is going and where the ion particle radiation is not going. Since the phantom form 250 is $EuD_4TEA$-inclusive and the tumor reproduction 1000R is $EuD_4TEA$-exclusive, a visible ion beam 500 ceases to be visible when it impinges upon tumor reproduction 1000R. Depending on the intensity of the ion beam 500 after having exited (completely passed through) the tumor reproduction 1000R, the ion beam 500 may become visible again (e.g., brightly visible, moderately visible, or slightly visible) or may remain invisible.

The intensity of the ion beam 500 is proportional to the $EuD_4TEA$-caused visibility of the ion beam 500. The more intense is the ion beam, the brighter is the ion beam. The brighter is the ion beam, the more intense is the ion beam. Decreased brightness of the ion beam implies decreased intensity of the ion beam. Decreased intensity of the ion beam implies decreased brightness of the ion beam. The inventive practitioner adjusts the beam to maximize the intensity of the radiation at the exact location of tumor reproduction 1000R, and to minimize the intensity of the radiation along the path of the beam other than this exact location of tumor reproduction 1000R. A paramount goal is to maximize the benefit of the radiation treatment in terms of defeating cancerous tissue, and to minimize the detriment of the radiation treatment in terms of damaging healthy tissue.

According to exemplary inventive practice of the second phantom mode, the ion beam 500 transmission is similarly directed through the interior of phantom form 250, with tumor reproduction 1000R in the direct path of ion beam 500. While traveling through a portion of the interior of phantom form 250, ion beam 500 is invisible until reaching tumor reproduction 1000R. When ion beam 500 impinges upon tumor reproduction 1000R, ion beam 500 appears inside phantom form 250 as a region of visible light corresponding to and coincident with tumor reproduction 1000R. Since phantom form 250 is $EuD_4TEA$-exclusive and tumor reproduction 1000R is $EuD_4TEA$-inclusive, ion beam 500 is invisible and becomes visible when it impinges upon tumor reproduction 1000R.

Inventive practice of medical phantoms 350 is capable of optimizing the radiation delivery to the real human patient 40 by experimentally defining, in advance of the radiation delivery, parameters including the patient 40's entry point (location) E of ion beam 500, the direction Ø of ion beam 500, the depth penetration p of ion beam 500, and the intensity of ion beam 500. For instance, the beam entry point E, the beam direction Ø, the depth penetration p, and the location (e.g., center or centroid) of the tumor reproduction 1000R may each be at least partially described in three dimensions, such as in three-dimensional Cartesian space. For instance, ion beam depth penetration p may be at least partially described in terms of the distance traveled by the beam between the human skin 41 surface and the tumor 1000, or the distance traveled by the beam between the human skin 41 surface and the endpoint of a beam segment that encompasses the tumor 1000 (such as shown in FIGS. 8 and 9). The empirical data that is inventively acquired using one or more phantoms 350 may thus be corresponded and translated to the ensuing actual delivery of the ion particle radiation to the patient.

Beam entry point E is the location at which ion beam 500 intersects the surface of the patient's skin 41, when ion beam 500 enters patient 40. According to some inventive embodiments, beam entry point E is predetermined (preselected), and the remaining parameters are then experimentally determined. For instance, a marker 150 may be initially placed on an inventive phantom 350, and then the inventive test simulation may be conducted. Marker 150 represents the entry point E of ion beam 500. The simulative determination of optimal parameters of the radiation delivery thus presupposes this location E of the phantom marker 150. According to other inventive embodiments, beam entry point E is among the parameters that are experimentally determined. According to exemplary inventive practice implementing inventive phantoms 350, the entry point E of the phantom 350 correlates to the marker 100 of the human 40. If such inventive practice involves preselection of the entry point E, a marker 150 may be used during the simulative testing to indicate the entry point E, which in turn correlates to the marker 100 of the human 40.

A proton beam (e.g., 250 MeV) is invisible to the naked eye. As such, according to conventional practice of ion beam therapy, theoretical calculations must be performed (e.g., by a medical physicist) to determine the location and direction of an ion beam inside a patient's body. Medical physicists currently base their calculations on a Bragg pattern. As compared with current oncological practice, the present invention is significantly advantageous in its ability to administer pinpoint delivery of radiation. In major contradistinction to conventional practice, a practitioner of the present invention can visually "see" an ion beam 500 through utilization of an inventive medical phantom 350, which contains $EuD_4TEA$ material. The inventive practitioner (e.g., medical physicist) can fine-tune the ion beam location and orientation/trajectory based on the visible light emitted by the $EuD_4TEA$.

According to exemplary inventive practice, when an ionization beam such as proton or carbon enters an inventive phantom, the beam distributes its energy in a Bragg pattern. This deposited energy interacts with the $EuD_4TEA$ material inside the inventive phantom 350, causing it to produce a visible red light. The amount of light produced is directly proportional to the amount of energy deposited. Since inventive phantom form 250 is transparent, an inventive practitioner (e.g., a medical physicist) may use this visible red light to fine-tune ion beam 500 such that the brightest spot of ion beam 500 is located on the cancerous entity (e.g., tumor) 1000. The path of ion beam 500 extends in a straight geometric line from accelerator 50 to and beyond tumor 1000 and continues outside the patient's head or body 40. Similarly, the path of ion beam 500 extends in a straight geometric line from accelerator 50 to and beyond tumor replica 1000R and continues outside phantom 350.

Variations in the intensity of beam 500 may manifest in $EuD_4TEA$-inclusive phantom 350 at every point along the path of beam 500, including before tumor 1000 impingement, during tumor 1000 impingement, and after tumor 1000 impingement. As a general rule for inventively administering radiation therapy to a living being, the less intense the beam radiation before and after hitting tumor 1000, the better. Tumor 1000 is the only location of the transmitting medium that is intended to be radiated. In fact, all of the non-malignant portions of the transmitting medium should not be radiated at all. As a practical matter in some inventive applications, a non-malignant portion of the transmitting medium cannot be entirely free of radiation when radiation is administered. In such cases, the inventive practitioner will usually strive, at least, to radiate the non-malignant portion as minimally as possible.

Multifarious embodiments and applications of the present invention are possible. Uniquely and with great effectiveness, the present invention avails itself of a distinctive capability of $EuD_4TEA$. In medical contexts such as cancer treatment involving radiation therapy, exemplary practice of the present invention uses $EuD_4TEA$-inclusive material as a beacon for proton therapy and other types of ion beam therapy. An entire working system according to the present invention may include, for example, an accelerator (e.g., cyclotron) and various feedback and control systems, which are employed based on signals received from an $EuD_4TEA$ beacon that guides as to where the ion beam is going and where the ion beam is not going.

The present invention, which is disclosed herein, is not to be limited by the embodiments described or illustrated herein, which are given by way of example and not of limitation. Other embodiments of the present invention will be apparent to those skilled in the art from a consideration of the instant disclosure or from practice of the present invention. Various omissions, modifications, and changes to the principles disclosed herein may be made by one skilled in the art without departing from the true scope and spirit of the present invention, which is indicated by the following claims.

What is claimed is:

1. A method for administering radiation therapy to a human or other animal, the method comprising:
   placing an $EUD_4TEA$-inclusive marker on an area of skin of said human or other animal;
   directing an ion beam toward said $EUD_4TEA$-inclusive marker so that at least a portion of said $EUD_4TEA$-inclusive marker luminesces;
   wherein said placing of said $EUD_4TEA$-inclusive marker is performed in accordance with a location of cancer;
   wherein said luminescence of said at least a portion of said $EUD_4TEA$-inclusive marker is associated with impingement of said ion beam upon said $EUD_4TEA$-inclusive marker.

2. The method for administering radiation therapy of claim 1, wherein said directing of said ion beam is performed so that at least a portion of said ion beam passes through said $EUD_4TEA$-inclusive marker and impinges upon said cancer.

3. A method for administering radiation therapy to a human or other animal, the method comprising:
   placing an $EUD_4TEA$-inclusive marker on an area of skin of said human or other animal;
   directing an ion beam toward said $EUD_4TEA$-inclusive marker so that at least a portion of said $EUD_4TEA$-inclusive marker luminesces;
   wherein said $EUD_4TEA$-inclusive marker includes a solid object;
   wherein said placing of said $EUD_4TEA$-inclusive marker includes adhering said $EUD_4TEA$-inclusive marker to said skin.

4. The method for administering radiation therapy of claim 3, wherein:
   said placing of said $EUD_4TEA$-inclusive marker is performed in accordance with a location of cancer;
   said luminescence of said at least a portion of said $EUD_4TEA$-inclusive marker is associated with impingement of said ion beam upon said $EUD_4TEA$-inclusive marker.

5. The method for administering radiation therapy of claim 4, wherein said directing of said ion beam is performed so that at least a portion of said ion beam passes through said $EUD_4TEA$-inclusive marker and impinges upon said cancer.

6. A method for administering radiation therapy to a human or other animal, the method comprising:
   placing an $EUD_4TEA$-inclusive marker on an area of skin of said human or other animal;
   directing an ion beam toward said $EUD_4TEA$-inclusive marker so that at least a portion of said $EUD_4TEA$-inclusive marker luminesces;
   wherein said $EUD_4TEA$-inclusive marker includes a gelatinous substance;
   wherein said placing of said $EUD_4TEA$-inclusive marker includes spreading said $EUD_4TEA$-inclusive marker upon said skin.

7. The method for administering radiation therapy of claim 6, wherein:
   said placing of said $EUD_4TEA$-inclusive marker is performed in accordance with a location of cancer;
   said luminescence of said at least a portion of said $EUD_4TEA$-inclusive marker is associated with impingement of said ion beam upon said $EUD_4TEA$-inclusive marker.

8. The method for administering radiation therapy of claim 7, wherein said directing of said ion beam is performed so that at least a portion of said ion beam passes through said $EUD_4TEA$-inclusive marker and impinges upon said cancer.

9. A method for performing radiation treatment, the method comprising:
   introducing an $EUD_4TEA$-inclusive material into at least one vessel in a tumorous region of a patient;
   directing an ion beam toward said tumorous region so that at least a portion of said $EUD_4TEA$-inclusive material luminesces in said at least one vessel.

* * * * *